(12) United States Patent
Wu et al.

US009248193B2

(10) Patent No.: US 9,248,193 B2
(45) Date of Patent: Feb. 2, 2016

(54) FORMULATIONS OF PHENYL URACIL COMPOUNDS

(75) Inventors: Huailiang Wu, Long Grove, IL (US);
Hao Hou, Waukegan, IL (US);
Adivaraha Jayasankar, Waukegan, IL (US); Ameesha Patel, Vernon Hills, IL (US); David Beno, New Albany, OH (US); Eric A. Schmitt, Libertyville, IL (US); Geoff G. Zhang, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 40 days.

(21) Appl. No.: 14/006,032

(22) PCT Filed: Mar. 16, 2012

(86) PCT No.: PCT/US2012/029478
§ 371 (c)(1),
(2), (4) Date: Nov. 4, 2013

(87) PCT Pub. No.: WO2012/129099
PCT Pub. Date: Sep. 27, 2012

(65) Prior Publication Data
US 2014/0378490 A1    Dec. 25, 2014

Related U.S. Application Data

(60) Provisional application No. 61/454,465, filed on Mar. 18, 2011.

(51) Int. Cl.
| | |
|---|---|
| *C07D 239/48* | (2006.01) |
| *A61K 47/38* | (2006.01) |
| *A61K 9/16* | (2006.01) |
| *A61K 9/20* | (2006.01) |
| *A61K 31/513* | (2006.01) |
| *A61K 9/48* | (2006.01) |
| *A61K 47/22* | (2006.01) |
| *A61K 47/26* | (2006.01) |
| *A61K 47/32* | (2006.01) |
| *A61K 9/14* | (2006.01) |

(52) U.S. Cl.
CPC ............... *A61K 47/38* (2013.01); *A61K 9/1611* (2013.01); *A61K 9/1617* (2013.01); *A61K 9/1635* (2013.01); *A61K 9/1652* (2013.01); *A61K 9/2013* (2013.01); *A61K 9/2018* (2013.01); *A61K 9/2027* (2013.01); *A61K 9/2054* (2013.01); *A61K 9/4858* (2013.01); *A61K 9/4866* (2013.01); *A61K 31/513* (2013.01); *A61K 47/22* (2013.01); *A61K 47/26* (2013.01); *A61K 47/32* (2013.01); *A61K 9/146* (2013.01)

(58) Field of Classification Search
CPC .............................. A61K 47/38; C07D 239/48
See application file for complete search history.

(56) References Cited

FOREIGN PATENT DOCUMENTS

| | | |
|---|---|---|
| WO | 2007109604 A2 | 9/2007 |
| WO | 2009039135 A1 | 3/2009 |
| WO | WO 2009039135 A1 * | 3/2009 |
| WO | 2010111348 A1 | 9/2010 |

OTHER PUBLICATIONS

International Seach Report for Application No. PCT/US2012/029478, mailed on Aug. 16, 2012, 3 pages.

* cited by examiner

*Primary Examiner* — Noble Jarrell
*Assistant Examiner* — John S Kenyon
(74) *Attorney, Agent, or Firm* — Neal, Gerber & Eisenberg LLP; Kevin A. O'Connor, Esq.

(57) ABSTRACT

A pharmaceutical product comprising at least one phenyl uracil-based pharmaceutically active agent or an agent of related structural type and processes for obtaining such product.

17 Claims, 11 Drawing Sheets

Figure 11. Compound A concentration in octanol phase following a 100 mg dose in bi-phasic dissolution testing.
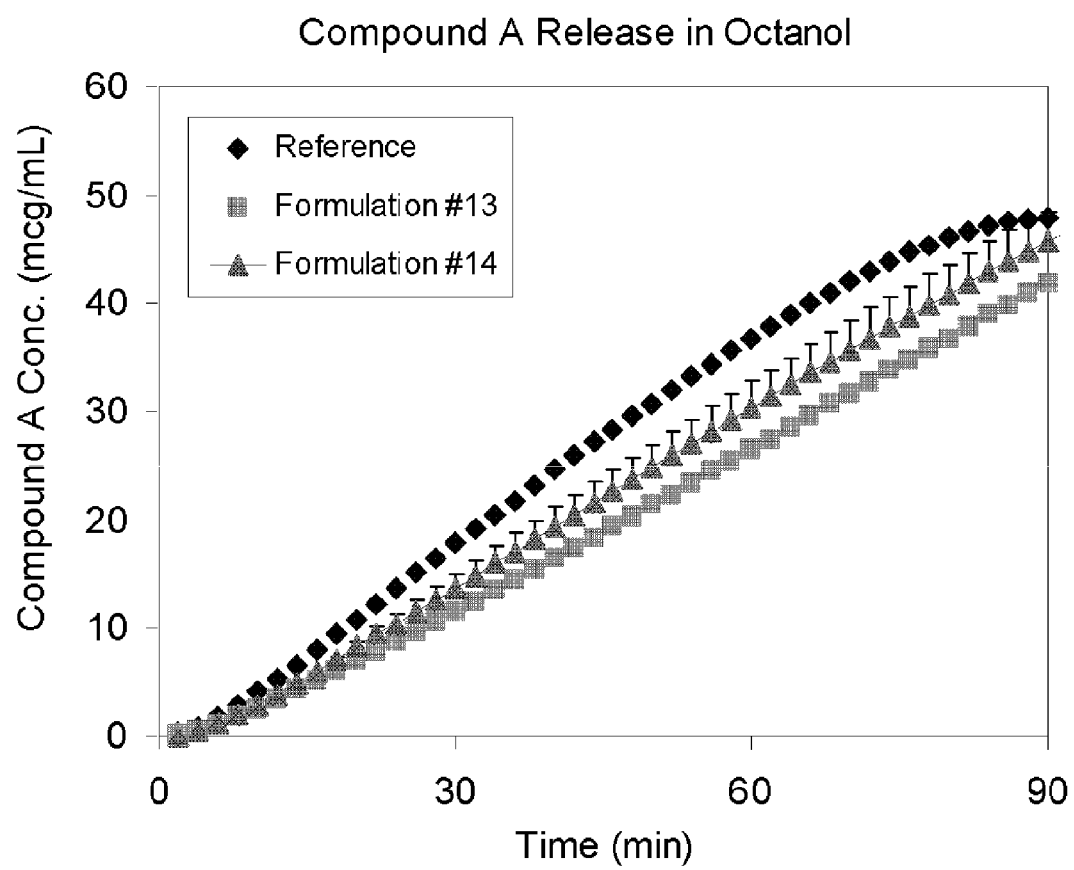

FORMULATIONS OF PHENYL URACIL COMPOUNDS

CROSS-REFERENCE TO RELATED APPLICATION

This application claims priority to U.S. Provisional Patent Application No. 61/454,465, filed on Mar. 18, 2011, the contents of which are herein fully incorporated by reference.

TECHNICAL FIELD

This disclosure is directed to: (a) pharmaceutical compositions of compounds of formula I that, inter alia, are useful for inhibiting hepatitis C virus (HCV); (b) processes for the preparation of the pharmaceutical compositions; and (c) methods of use of such compositions.

BACKGROUND

One of the common problems of poorly water-soluble drugs is that they provide low bioavailability and/or higher variability in bioavailability as a result of poor water solubility and slow dissolution. Formation of a soluble salt form for an insoluble compound is often a means to increase drug solubility in an aqueous medium, and hence improve dissolution rate and ultimately enhance bioavailability. In some cases, even a soluble salt of a drug has high bio-variability and/or poor bioavailability. For example, upon exposure to aqueous medium, the salt may undergo a dissolution process during which the solid particle dissolves and then diffuses. However, during the dissolution process, the salt can be dissociated to a non-ionized form. The non-ionized form may achieve supersaturation and then precipitate out either on the exterior surface of the salt particle or in the bulk medium. This prevents further dissolution of the salt, and results in low bioavailability with high variability.

It is also desirable to deliver a pharmaceutical composition to a patient as a tablet or capsule, which may provide greater chemical stability and improved patient convenience compared to semi-solid or solution dosage forms.

There is, therefore, a need for improved formulations of water-insoluble drugs and, in particular, improved formulations of phenyl uracil compounds such as (E)-N-(4-(3-tert-butyl-5-(2,4-dioxo-3,4-dihydropyrimidin-1(2H)-yl)-2-methoxystyryl)phenyl)methanesulfonamide and its salts.

SUMMARY OF THE INVENTION

The disclosure is directed to formulations of and pharmaceutical compositions comprising phenyl uracil compounds including compounds having the structure of formula I, also known as (E)-N-(4-(3-tert-butyl-5-(2,4-dioxo-3,4-dihydropyrimidin-1(2H)-yl)-2-methoxystyryl)phenyl)methanesulfonamide, or salts or crystalline forms thereof. The salts and crystalline forms may include, for example, those as described in International Publication No. WO2009/039127, such as sodium salts, potassium salts, and choline salts, and crystalline forms, such as solvate and hydrate forms, and their salts as well as solvent-free crystalline forms and their salts. As referred to herein, compound A is the potassium salt of (E)-N-(4-(3-tert-butyl-5-(2,4-dioxo-3,4-dihydropyrimidin-1(2H)-yl)-2-methoxystyryl)phenyl)methanesulfonamide.

This disclosure is also directed to methods of improving dissolution rate and the extent of dissolution as well as enhancing bioavailability of phenyl uracil compounds such as (E)-N-(4-(3-tert-butyl-5-(2,4-dioxo-3,4-dihydropyrimidin-1(2H)-yl)-2-methoxystyryl)phenyl)methanesulfonamide. In particular, the disclosure is directed to methods of improving dissolution rate and the extent of dissolution of phenyl uracil compounds such as (E)-N-(4-(3-tert-butyl-5-(2,4-dioxo-3,4-dihydropyrimidin-1(2H)-yl)-2-methoxystyryl)phenyl)methanesulfonamide from solid dosage forms such as a tablet, and methods of enhancing in vivo bioavailability of the compounds.

It has been surprisingly found that stable amorphous solid dispersion (ASD) powders of the drug (free acid or salts) using different polymers and surfactants at various levels of each ingredient substantially prevent the salt form of the compound from being dissociated to a non-ionized form and enhance the rate and extent of drug dissolution and, consequently, the bioavailability of the compounds. By preparation of a stable ASD formulation of the insoluble compound, the aqueous (apparent) solubility of the compound is increased. As a result of achieving significantly higher solubility, the dissolution rate/extent in the dissolution media both in vitro and in vivo is increased. Therefore, the oral absorption and oral bioavailability is enhanced.

It has also been found that modifying the pH of a diffusion layer of a dosage form with certain alkalizing agents prevents the salt form of the compounds from being dissociated to a non-ionized form and enhances the rate and extent of drug dissolution and, consequently, the bioavailability of the compounds.

The disclosure provides pharmaceutical products comprising a phenyl uracil compound. The composition is obtained by preparing a liquid mixture comprising the compound, at least one surfactant, at least one polymer and at least one solvent; removing the solvent from the liquid mixture to obtain a solid dispersion product; and combining the solid dispersion product with at least one pharmaceutically acceptable excipient.

The disclosure provides methods for preparing a pharmaceutical product comprising a phenyl uracil compound, wherein the method comprises preparing a liquid mixture comprising the phenyl uracil compound, at least one surfactant, at least one polymer and at least one solvent; removing the solvent from the liquid mixture to obtain a solid dispersion product; and combining the solid dispersion product with at least one pharmaceutically acceptable excipient.

The disclosure provides pharmaceutical products comprising a phenyl uracil compound, at least one alkalizing agent having a pKa value greater than the pKa of the phenyl uracil compound; at least one water-soluble low molecular weight polymer to inhibit crystallization growth, and at least one surfactant.

The composition is obtained by maintaining high pH in the diffusion layer by adding at least one alkalizing agent having a pKa value greater than the pKa of the phenyl uracil compound; 2) using a water soluble low molecular weight polymer to inhibit crystallization growth, such as CoPVP, PVP, HPMC, HPC, and other suitable polymers; 3) increasing the concentration of the drug in the diffusion layer; 4) increasing wettability of the drug/formulation by mixing surfactants such as Vitamin E TPGS, SDS, polysorbate and poloxamer; 4) increasing active pharmaceutical ingredient (API) surface area by reducing particle size; 5) using a wet granulation process to mix the drug with excipients to foster intimate interaction, and combinations thereof; and combining the solid dispersion product with at least one pharmaceutically acceptable excipient.

The disclosure provides methods for preparing a pharmaceutical product comprising a phenyl uracil compound, wherein the method comprises maintaining high pH in the diffusion layer; inhibiting crystallization growth; increasing the concentration of the phenyl uracil compound in the diffusion layer; increasing wettability of the phenyl uracil compound; reducing particle size of the phenyl uracil compound; and combining the with at least one pharmaceutically acceptable excipient.

In embodiments, the disclosure provides methods of preparing a pharmaceutical composition comprising a phenyl uracil compounds. The method includes combining into a mixture the phenyl uracil compound with at least one alkalizing agents having pKa values greater than the pKa of the phenyl uracil compound, at least one water soluble low molecular weight polymer and at least one surfactant; and combining the mixture with at least one pharmaceutically acceptable excipient.

BRIEF DESCRIPTION OF THE DRAWINGS

FIG. 11 is a graph illustrating bi-phasic dissolution of Compound A in octanol following a 100 mg dose.

DETAILED DESCRIPTION

Figure 1:
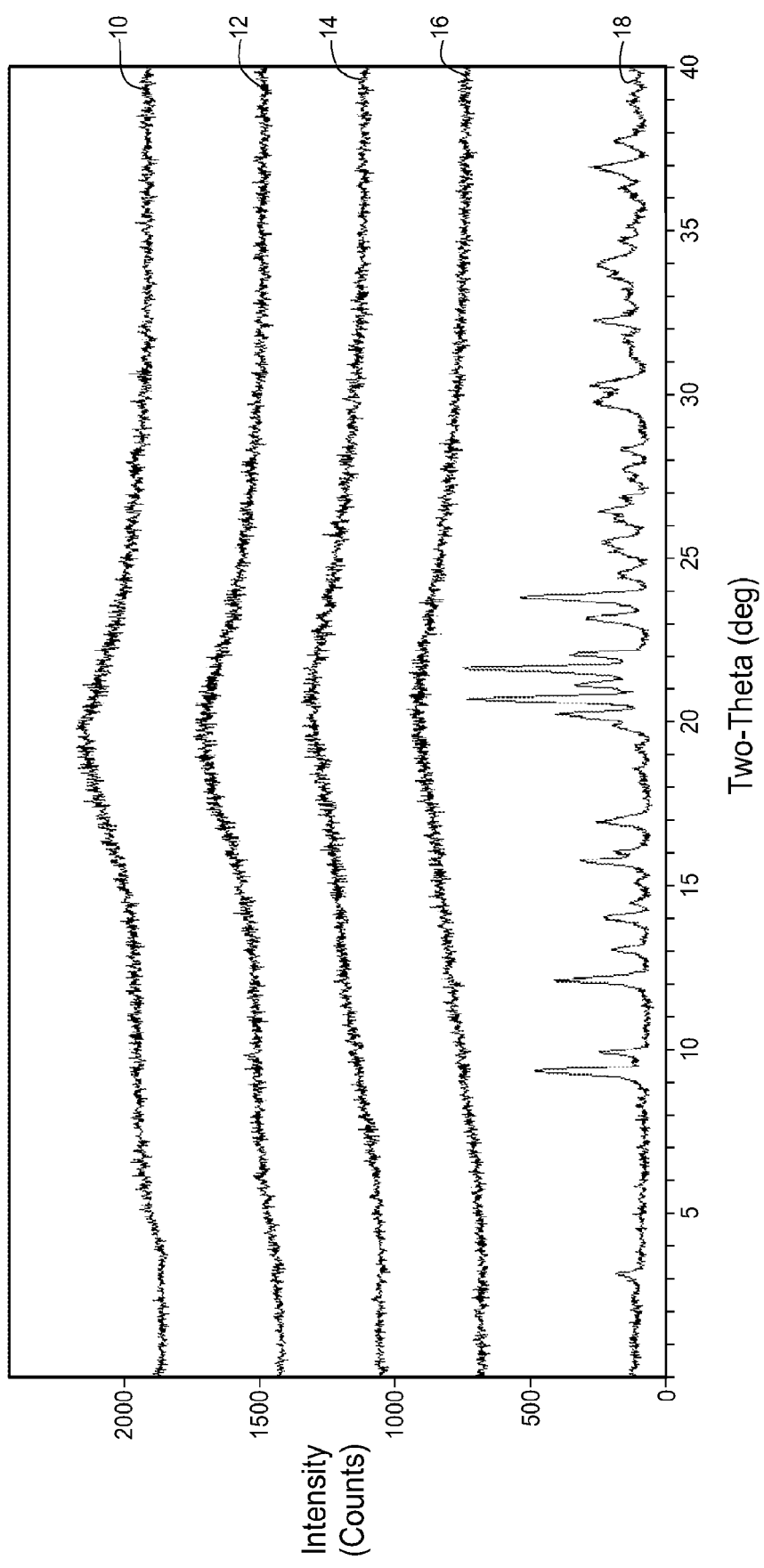
FIG. 1 is a graph illustrating an XRPD pattern of exemplary formulations of Compound A.

This disclosure is directed to formulations of phenyl uracil-based active agents. The phenyl uracil active agents are biologically active compounds which are comprised of a uracil moiety in their molecular structure wherein one nitrogen atom is attached to the phenyl moiety, and which exert a local physiological effect, as well as those which exert a systemic effect, after oral administration. The phenyl group is substituted by further substituents. In particular, the disclosure is directed to formulations of and pharmaceutical compositions comprising compounds having the structure of formula I—(E)-N-(4-(3-tert-butyl-5-(2,4-dioxo-3,4-dihydropyrimidin-1(2H)-yl)-2-methoxystyryl)phenyl)methanesulfonamide—or salts or crystalline forms thereof.

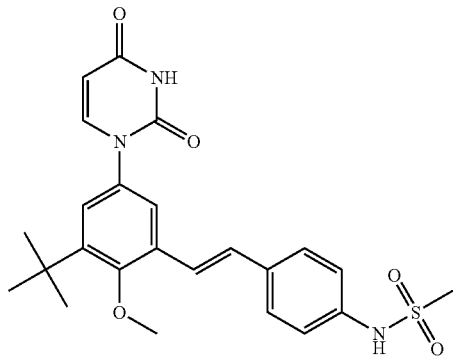

(I)

Salts.

This disclosure also is directed, in part, to all salts of the compounds of formula I. A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula I can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula I include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

The salts and crystalline forms may include those as described in, for example, International Publication No. WO2009/039127, such as sodium salts, potassium salts, and choline salts, and crystalline forms and their salts such as solvate and hydrate forms as well as solvent-free crystalline forms and their salts.

In embodiments, the salt is a potassium salt of (E)-N-(4-(3-tert-butyl-5-(2,4-dioxo-3,4-dihydropyrimidin-1(2H)-yl)-2-methoxystyryl)phenyl)methanesulfonamide.

In embodiments, the salt is a monopotassium salt of (E)-N-(4-(3-tert-butyl-5-(2,4-dioxo-3,4-dihydropyrimidin-1(2H)-yl)-2-methoxystyryl)phenyl)methanesulfonamide (Compound A).

Isomers.

This disclosure also is directed, in part, to all isomers of the compounds of formula I (and their salts) (i.e., structural and stereoisomers). Structural isomers include chain and position isomers. Stereoisomers include E/Z isomers (i.e., isomers with regard to one or more double bonds), enantiomers (i.e., stereoisomers that have opposite configurations at all stereogenic centers), and diastereoisomers (i.e., stereoisomers that have the same configuration at one or more stereogenic centers, but differ at other stereogenic centers).

Amorphous Solid Dispersion Formulations

The disclosure provides pharmaceutical products comprising a phenyl uracil compound. The composition is obtained by preparing a liquid mixture comprising the compound, at least one surfactant, at least one polymer and at least one solvent; removing the solvent from the liquid mixture to obtain a solid dispersion product; and combining the solid dispersion product with at least one pharmaceutically acceptable excipient.

The disclosure provides methods for preparing a pharmaceutical product comprising a phenyl uracil compound, wherein the method comprises preparing a liquid mixture comprising the phenyl uracil compound, at least one surfactant, at least one polymer and at least one solvent; removing the solvent from the liquid mixture to obtain a solid dispersion product; and combining the solid dispersion product with at least one pharmaceutically acceptable excipient.

Stable amorphous solid dispersion powders are obtained by vacuum-drying or spray-drying solutions containing dissolved active agent (free acid or salt), polymers and surfactants at various levels.

In embodiments, the pharmaceutical product comprising a phenyl uracil derivative active agent is formulated as an amorphous solid dispersion prior to undergoing further processing.

The post-dried solid dosage formulations (tablets and capsules) are prepared by directly blending the amorphous solid dispersion powders with other commonly used pharmaceutical grade excipients through processes such as direct blending or roller compaction. The compositions are then compressed into tablets or encapsulated into capsules.

In embodiments, the amorphous solid dispersion formulation of the active agent is prepared by a process using at least one polymer and at least one surfactant. The process includes dissolving the polymer, surfactant and the active agent in a solvent, removing the solvent and collecting the residual solid.

In embodiments, about 60% to about 80% of the weight of the formulation is polymer. The polymers may include, for example, at least one of copovidone; polyvinylpyrrolidone (PVP) such as PVPK30, (hydroxypropyl)methyl cellulose (HPMC) such as HPMCE5, HPMC-AS, and HPMC-P55; hydroxypropyl cellulose (HPC); or any other suitable polymer.

In embodiments, about 5% to about 10% of the weight of the formulation is surfactant. The surfactants may include, for example, vitamin E d-alpha tocopheryl polyethylene glycol succinate (Vit E TPGS), sodium dodecyl sulfate (SDS), polysorbate, poloxamer, sorbitan laurate such as Span™ 20, polyoxyethylene sorbitan monolaurate such as Tween® 20, or any other suitable surfactant.

In embodiments, about 60% to about 80% of the weight of the formulation is polymer selected from copovidone or HPMC, and about 5% to about 10% of the weight of the formulation is Vit E TPGS. In embodiments about 60% to about 80% of the weight of the formulation is copovidone, and about 5% to about 10% of the weight of the formulation is Vit E TPGS. In embodiments about 60% to about 80% of the weight of the formulation is HPMC, and about 5% to about 10% of the weight of the formulation is Vit E TPGS.

The polymer, surfactant and the active agent may be dissolved separately or together. In embodiments, the polymer, surfactant and the active agent are dissolved together in a solvent. In embodiments, the polymer and surfactant are dissolved in a solvent, and the active agent is added to the polymer/surfactant solution.

Suitable solvents are those which are capable of substantially dissolving or substantially solubilizing the polymer, surfactant and the active agent. Typically, non-aqueous solvents are used. Any such solvent may be used; however, pharmaceutically acceptable solvents are preferred because traces of solvent may remain in the dried solid dispersion product. The solvent may be selected from the group consisting of alkanols, such as methanol, ethanol, isopropanol, n-propanol, isobutanol, n-butanol; hydrocarbons, such as pentane, hexane, cyclohexane, methylcyclohexane, toluene, xylene; halogenated hydrocarbons, such as dichloromethane, trichloromethane, dichloroethane, chlorobenzene; ketones, such as acetone; esters, such as ethyl acetate; ethers, such as dioxane, tetrahydrofuran; and combinations of two or more thereof. The solvents may include any suitable solvent such as one or more organic solvents, one or more aqueous solvents or mixtures thereof. For example, the solvent may include one or more of ethanol, water-acetone mixture and water-ethanol mixture. In embodiments, the solvent is ethanol. In embodiments, the solvent is a water-acetone mixture. In embodiments, the polymer, surfactant and the active agent are dissolved in a 1:4 (v/v) water-acetone mixture. In embodiments, the solvent is a water-ethanol mixture. In embodiments, the polymer, surfactant and the active agent are dissolved in a 1:8 (v/v) water-ethanol mixture.

The liquid mixture may be prepared by any suitable method of contacting each of the active agent, one or more polymers, one or more surfactants and one or more solvents. In addition, the dissolution of the mixture may be enhanced by agitation such as by stirring or sonication. In an embodiment, the liquid mixture is prepared by dissolving the pharmaceutically acceptable matrix-forming agent to obtain a matrix-forming agent solution, and adding the active agent and the pharmaceutically acceptable surfactant to the solution. The dissolved matrix-forming agent may exert a solubility-enhancing effect on the active agent; thus, the solubility of the active agent in the matrix-forming agent solution may be several times higher than its solubility in the solvent alone. The active agent may be substantially dissolved in the liquid mixture.

The liquid mixture may have a dry matter content of up to about 90% by weight, for example, from about 0.5 to about 90% by weight or from about 2 to about 60% by weight, relative to the total weight of the liquid mixture.

At least one filler may be added to the liquid mixture before removing the solvent(s).

The solvent(s) may be removed by any suitable method known in the art, such as spray-drying, drum drying, belt drying, tray drying, fluid-bed drying or combinations of two or more thereof. For example, the primary solid dispersion powder obtained by spray-drying may be further dried by tray drying (optionally under vacuum) or fluid-bed drying (optionally under vacuum).

In an embodiment, removal of the solvent comprises a spray-drying step, optionally in combination with one or more drying steps other than spray-drying. The solvent may be removed from the mixture by any suitable method such as one or more of the following techniques: heating, passing the mixture through a mesh screen and drying such as vacuum drying and spray drying. In embodiments, the mixture is heated at a temperature of about 75° C. and dried at a temperature of about 60° C. to about 75° C.

The residual solvent content in the final solid dispersion product may be about 5% by weight or less, or about 1% by weight or less.

The drum drying process (roller drying) includes applying a thin film of material to the smooth surface of a continuously rotating, heated metal drum. The film of dried material is continuously scraped off by a stationary knife located opposite the point of application of the liquid material. The dryer consists of a single drum or a pair of drums with or without "satellite" rollers. The drum(s) may be located in a vacuum chamber. The solvent vapors are collected and the solvent is recovered and recycled.

In a belt dryer, the liquid is spread or sprayed onto a belt which passes over several heated plates underneath the belt. The material is heated by steam-heated or electrically heated plates. The evaporation of the solvent can additionally be fostered by infrared radiators or microwave radiators located over the belt. Belt drying may be carried out in a vacuum chamber.

In tray drying, the liquid mixture (or a dispersion product that has been pre-dried by any other method) is distributed over a number of trays. These are placed in an oven, usually in a stream of hot gas, e.g. air. Vacuum may be applied additionally.

In spray-drying, the liquid to be dried is suspended in a gas flow, e.g., air, i.e. the liquid is converted into a fog-like mist (atomized), providing a large surface area. The atomized liquid is exposed to a flow of hot gas in a drying chamber. The moisture evaporates quickly and the solids are recovered as a powder consisting of fine, hollow spherical particles. Gas inlet temperatures of up to 250° C. or even higher may be used, due to the evaporation the gas temperature drops very rapidly to a temperature of about 30 to 150° C. (outlet temperature of the gas).

In embodiments, the mixture is spray dried. In such embodiments, the polymer, surfactant, active agent solution is fed through a sprayer where it is heated at the inlet of the sprayer and cooled at the outlet of the sprayer. The solution is fed through the sprayer at a feed rate of about 2 ml/min. The inlet temperature of the sprayer may be about 80° C. to about 115° C. The outlet temperature of the sprayer may be about 30° C. to about 70° C.

The solids collected from spray drying may be further dried. For example, in embodiments, the collected solids are dried in a vacuum oven overnight at about 31° C.

The dried solid dispersion product may then be ground and/or classified (sieved).

The dried solid dispersion product may then be filled into capsules or may be compacted. Compacting means a process whereby a powder mass comprising the solid dispersion product is densified under high pressure in order to obtain a compact with low porosity, e.g. a tablet. Compression of the powder mass is usually done in a tablet press, more specifically in a steel die between two moving punches.

Table 1 below describes the percentage of the active agent, Compound A, surfactant and polymer in exemplary amorphous solid dispersion formulations.

TABLE 1

| ASD Formulation | | A | B | C | D | E | F | G | H | I | J | K | L | M | N |
|---|---|---|---|---|---|---|---|---|---|---|---|---|---|---|---|
| Active Agent | Compound A | 15 | 15 | 25 | 25 | 25 | 30 | 30 | 30 | 30 | 30 | 30 | 30 | 30 | 25 |
| Surfactant | Vit E/TPGS | 10 | 5 | 10 | 5 |  | 10 |  |  | 10 |  |  |  |  | 10 |
|  | Span™ 20 |  |  |  |  |  |  | 10 |  |  | 10 |  |  |  |  |
|  | Tween® 20 |  |  |  |  |  |  |  | 10 |  |  | 10 |  |  |  |
|  | Tween® 80 |  |  |  |  | 10 |  |  |  |  |  |  |  |  |  |
| Polymer | Copovidone | 75 | 80 | 65 | 70 | 65 | 60 | 60 | 60 |  |  |  |  |  |  |
|  | HPMC-E5 |  |  |  |  |  |  |  |  | 60 | 60 | 60 | 70 |  | 65 |
|  | HPMC-P55 |  |  |  |  |  |  |  |  |  |  |  |  | 70 |  |
| Total | | 100 | 100 | 100 | 100 | 100 | 100 | 100 | 100 | 100 | 100 | 100 | 100 | 100 | 100 |

Table 2 below describes various solvents used in preparing exemplary ASD formulations. PVP-K30 or HPMC AS polymer with Tween® 20 or Span™ 20 surfactants for 15% and 25% drug loadings.

TABLE 2

| Composition | Solvent |
|---|---|
| 25% Compound A (21% free acid), 10% Vit E TPGS, 65% copovidone | ethanol |
| 25% Compound A (21% free acid), 10% Vit E TPGS, 65% copovidone | 1:8 water-ethanol |
| 30% Compound A (25% free acid), 10% Tween ® 20, 60% copovidone | 1:8 water-ethanol |
| 30% Compound A (25% free acid), 10% Span ™ 20, 60% copovidone | 1:8 water-ethanol |
| 30% Compound A (25% free acid), 10% Vit E TPGS, 60% copovidone | 1:8 water-ethanol |
| 30% Compound A (25% free acid), 10% Tween ® 20, 60% HPMC E5 | 1:8 water-ethanol |
| 30% Compound A (25% free acid), 10% Tween ® 20, 60% HPMC E5 | 1:8 water-ethanol |
| 30% Compound A (25% free acid), 10% Vit E TPGS, 60% HPMC E5 | 1:8 water-ethanol |
| 30% Compound A (25% free acid), 10% Span ™ 20, 60% HPMC E5 | 1:8 water-ethanol |
| 30% Compound A (25% free acid), 10% TPGS, 60% copovidone | 1:8 water-ethanol |
| 30% Compound A (25% free acid), 5% TPGS, 65% copovidone | 1:8 water-ethanol |
| 17.9% Compound A (15% free acid), 10% TPGS, 72.1% copovidone | 1:8 water-ethanol |
| 17.1% Compound A (14.3% free acid), 5% TPGS, 77.9% copovidone | 1:8 water-ethanol |
| 30% Compound A (25% free acid), 10% Tween ® 80, 60% copovidone | 1:8 water-ethanol |
| 30% Compound A (25% free acid), 70% HPMC E5 | 1:8 water-ethanol |
| 30% Compound A (25% free acid), 70% HPMC P55 | 1:4 water-acetone |
| 17.9% Compound A (15% free acid), 5% TPGS, 77.1% copovidone | 1:8 water-ethanol |
| 30% Compound A (25% free acid), 10% Vit E TPGS, 60% HPMC E5 | 1:8 water-ethanol |

The exemplary ASD formulations were found to be stable through at least 3 months. Physical stability of certain amorphous solid dispersions was assessed under packaged conditions for up to 3 months. The packaged samples had 1-2 gram silica gel as desiccant in 5 oz HDPE heat inductions sealed bottles. The sample containing bottles were stored at 25° C. and 60% relative humidity. Table 3 summarizes the physical stability data of exemplary ASD formulations.

Figure 2:
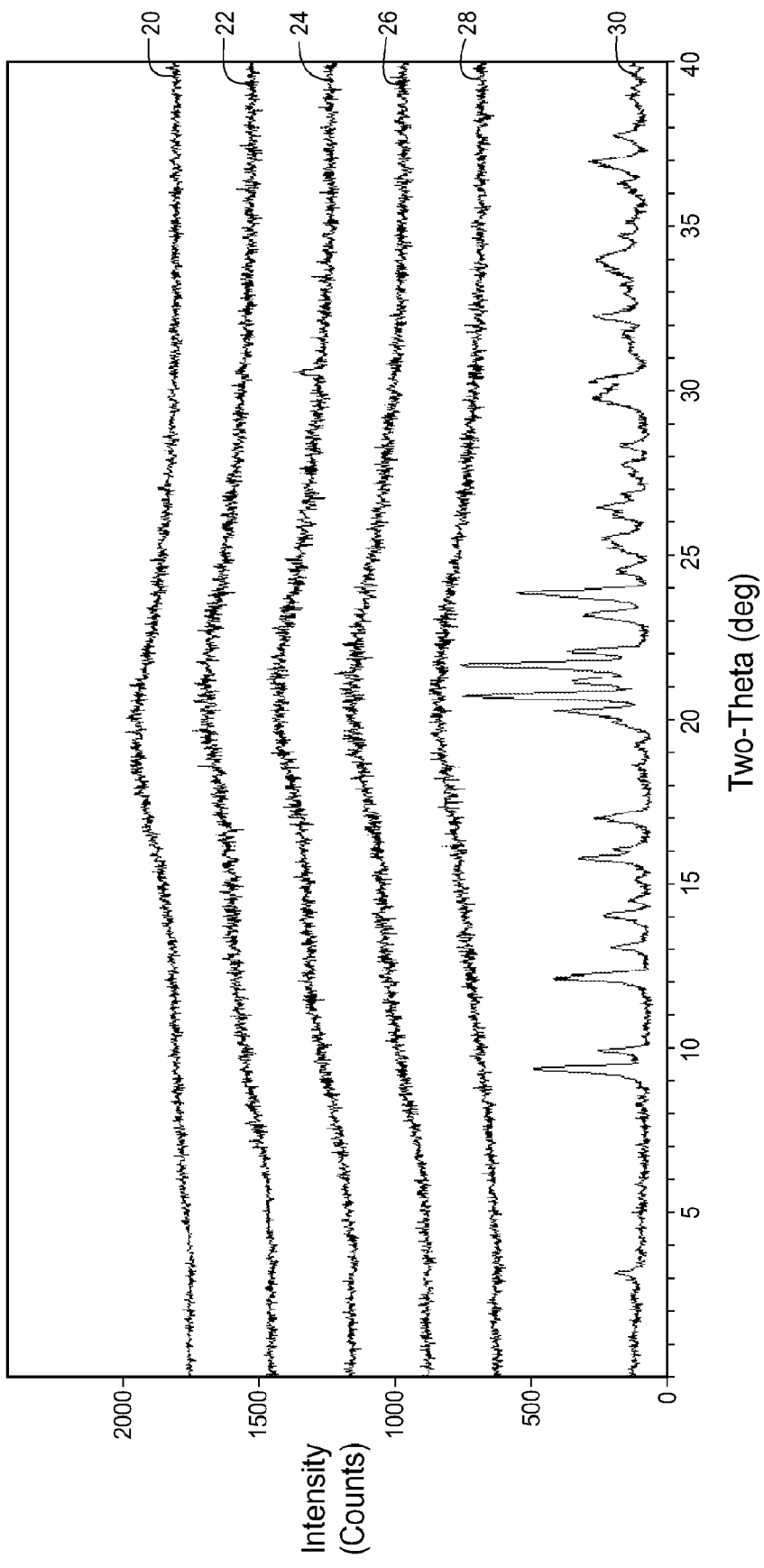
FIG. 2 is a graph illustrating an XRPD pattern of exemplary formulations of Compound A.

FIG. 2 shows the XRPD patterns of amorphous solid dispersions of Compound A formulations by spray dying solutions containing HPMC E5 or copovidone with Vit E TPGS and 17.94% or 29.90% salt active agent. XRPD patterns of Compound A spray dried solid dispersions. In particular, sample 20 includes 29.90% Compound A (25% free acid), 10% Vit E TPGS, and HPMC E5; sample 22 includes 17.9% Compound A (15% free acid), 5% TPGS, copovidone;

| Solid Dispersion | 2 week | 4 week | 3 month |
|---|---|---|---|
| 25% Compound A, 10% Vit E TPGS, 65% copovidone | STABLE | STABLE | STABLE |
| 30% Compound A, 10% Span ™ 20, 60% copovidone | STABLE | not tested | STABLE |
| 30% Compound A, 10% Tween ® 20, 60% copovidone | STABLE | STABLE | STABLE |
| 30% Compound A, 10% Vit E TPGS, 60% copovidone | STABLE | STABLE | STABLE |
| 30% Compound A, 10% Tween ® 20, 60% HPMC-E5 | STABLE | STABLE | STABLE |
| 30% Compound A, 10% Vit E TPGS, 60% HPMC-E5 | STABLE | STABLE | STABLE |
| 30% Compound A, 10% Span ™ 20, 60% HPMC-E5 | STABLE | STABLE | STABLE |
| 25% Compound A, 5% Vit E TPGS, 70% copovidone | STABLE | STABLE | STABLE |
| 15% Compound A, 10% Vit E TPGS, 75% copovidone | STABLE | STABLE | STABLE |
| 15% Compound A, 5% Vit E TPGS, 80% copovidone | STABLE | not tested | STABLE |
| 25% Compound A, 10% Tween ® 20, 65% copovidone | STABLE | STABLE | STABLE |
| 30% Compound A, 70% HPMC-P55 | not tested | not tested | STABLE |

XRPD confirmed that Compound A remained in amorphous in various formulations. FIG. 1 shows the XRPD patterns of amorphous solid dispersions of Compound A formulations by vacuum drying solutions using HPMC E5 or copovidone and Vit E TPGS. In particular, sample 10 includes 10% Vit E TPGS, 15% Compound A (free acid) and HPMC E5; sample 12 includes 25% Compound A (free acid) and HPMC E5; sample 14 includes 15% Compound A (free acid) and copovidone; sample 16 includes 25% Compound A (free acid) and copovidone; and sample 18 is Compound A alone. The powder patterns indicate that the solid phases are amorphous. Amorphous dispersions were also obtained using sample 24 includes 17.1% Compound A (14.3% free acid), 5% TPGS, copovidone; sample 26 includes 17.9% Compound A (15% free acid), 10% TPGS, copovidone; sample 28 includes 30% Compound A (25% free acid), 10% Vit E TPGS, copovidone; and sample 30 is Compound A. The powder patterns confirm that the solid phases are amorphous.

In vivo bioavailability studies were conducted on ASD formulations B, C, E and N encapsulated and dosed in 16 dogs. Each formulation, with Compound A equivalent to 25 mg free acid, was dosed in 4 dogs. All dogs were also dosed with phosal lipid-based liquid formulation containing the drug as a reference.

| ASD Formulation | | A | B | C | D | E | F | G | H | I | J | K | L | M | N |
|---|---|---|---|---|---|---|---|---|---|---|---|---|---|---|---|
| Active Agent | Compound A | 15 | 15 | 25 | 25 | 25 | 30 | 30 | 30 | 30 | 30 | 30 | 30 | 30 | 25 |
| Surfactant | Vit E/TPGS | 10 | 5 | 10 | 5 | | 10 | | | 10 | | | | | 10 |
| | Span ™ 20 | | | | | | | 10 | | | 10 | | | | |
| | Tween ® 20 | | | | | | | | 10 | | | 10 | | | |
| | Tween ® 80 | | | | | 10 | | | | | | | | | |

-continued

| ASD Formulation | A | B | C | D | E | F | G | H | I | J | K | L | M | N |
|---|---|---|---|---|---|---|---|---|---|---|---|---|---|---|
| Polymer Copovidone | 75 | 80 | 65 | 70 | 65 | 60 | 60 | 60 | | | | | | |
| HPMC-E5 | | | | | | | | | 60 | 60 | 60 | 70 | | 65 |
| HPMC-P55 | | | | | | | | | | | | | 70 | |
| Total | 100 | 100 | 100 | 100 | 100 | 100 | 100 | 100 | 100 | 100 | 100 | 100 | 100 | 100 |

Amorphous Solid Dispersion Formulations:

B: 15% Compound A (free acid basis), 5% Vit E TPGS, copovidone
C: 25% Compound A (free acid basis), 10% Vit E TPGS, copovidone
E: 25% Compound A (free acid basis), 10% Tween ® 80, copovidone
N: 25% Compound A (free acid basis), 10% Vit E TPGS, HPMC E5

Table 4 shows the Cmax, AUC, and Tmax obtained for four solid dispersions compared to standard lipid-based liquid formulations (phosal solutions) after dosing in dogs. The AUC values of the 4 formulations are not significantly different after considering the variability. However, based on mean AUC values, formulations B and N appear to show the higher bioavailability among the four amorphous solid dispersion formulations.

TABLE 4

| Dogs | Formulation | $t_{1/2}$ | AUC | $C_{max}$ | $T_{max}$ |
|---|---|---|---|---|---|
| 5-8 | B | 8.7 hours | 18.65 (4.94) | 1.78 (0.43) | 1.5 (0.0) |
| | Phosal | 8.4 hours | 26.98 (6.42) | 1.92 (0.42) | 2.5 (0.3) |
| 1-4 | C | 8.0 hours | 12.79 (3.32) | 1.33 (0.40) | 2.8 (0.3) |
| | Phosal | 8.6 hours | 22.97 (5.08) | 1.75 (0.36) | 2.8 (0.5) |
| 9-12 | E | 6.3 hours | 14.39 (2.75) | 1.47 (0.30) | 1.8 (0.4) |
| | Phosal | 8.2 hours | 25.40 (4.86) | 1.97 (0.37) | 2.8 (0.3) |
| 13-16 | N | 5.8 hours | 20.13 (2.59) | 2.01 (0.34) | 1.8 (0.8) |
| | Phosal | 10.1 hours | 28.45 (5.24) | 1.81 (0.24) | 2.8 (0.3) |

The solid dispersion product may be further processed to produce a pharmaceutical product. The pharmaceutical product may be prepared by any suitable process such as direct blending, roller compaction and combinations thereof. The granulation may be mixed with extragranular excipients, and the final blend compressed into tablets, filled into capsules or prepared as other solid dosage forms for oral administration including, for example, as powders and granules.

a. Direct Blending

In embodiments, the solid dispersion product undergoes direct blending together with excipients followed by compression into tablets or encapsulation into capsules. In embodiments, the excipients may include one or more fillers, disintegrant, lubricants and any other suitable excipients or combinations thereof.

Fillers may include, for example, microcrystalline cellulose, such as Avicel® PH102, lactose monohydrate, such as lactose monohydrate Fast Flo® 316, and other suitable fillers. At least about 25% to about 90% w/w or from about 30% to about 85% w/w of the pharmaceutical product may be filler. In embodiments, excipients include no filler. In embodiments, excipients include about 30% filler. In embodiments, excipients include about 45% filler. In embodiments, excipients include about 60% filler. In embodiments, intragranular excipients include about 65% filler. In embodiments, intragranular excipients include about 75% filler. In embodiments, intragranular excipients include about 80% filler.

The pharmaceutical product may include a combination of fillers such as a combination of microcrystalline cellulose and lactose monohydrate in substantially the same or different amounts of each excipient. At least about 20% to about 65% w/w or from about 25% to about 60% w/w of the pharmaceutical product may be microcrystalline cellulose, and at least about 20% to about 50% w/w or from about 25% to about 45% w/w of the pharmaceutical product may be lactose monohydrate. In embodiments, excipients include about 28% microcrystalline cellulose and about 28% lactose monohydrate. In embodiments, excipients include about 30% microcrystalline cellulose and about 30% lactose monohydrate. In embodiments, excipients include about 33% microcrystalline cellulose and about 33% lactose monohydrate. In embodiments, excipients include about 40% microcrystalline cellulose and about 40% lactose monohydrate. In embodiments, intragranular excipients include about 42% microcrystalline cellulose and about 42% lactose monohydrate.

Disintegrants may include, for example, cross-linked sodium carboxymethylcellulose, such as sodium croscarmellose or any other suitable disintegrant in any suitable amounts including, for example, from about 2% to about 10% w/w of the pharmaceutical product. In embodiments, excipients include about 5% disintegrant.

Lubricants may include, for example, sodium stearyl fumarate, colloidal silicon dioxide or any other suitable lubricants. At least about 1% to about 3% w/w of the pharmaceutical product may be lubricant. In embodiments, excipients include no lubricant. In embodiments, excipients include about 3% lubricant. The pharmaceutical product may include a combination of lubricants such as a combination of colloidal silicon dioxide and sodium stearyl fumarate in substantially the same or different amounts of each excipient. At least about 0.5% to about 2% w/w of the pharmaceutical product may be colloidal silicon dioxide, and at least about 1% to about 3% w/w of the pharmaceutical product may be sodium stearyl fumarate. In embodiments, excipients include about 1% colloidal silicon dioxide and about 2% sodium stearyl fumarate.

Table 5 presents examples of the disclosed formulations prepared by direct blending of the solid dispersion product with excipients and encapsulating the final blend into capsules. In particular, Table 5 presents the percentage of components by weight (w/w) of capsule formulations of 25 mg and 50 mg dosages of Compound A.

TABLE 5

| | | Post-ASD Formulation | | | |
|---|---|---|---|---|---|
| | | 1 | 2 | 7 | 8 |
| ASD Formulation | | a | a | b | b |
| Dose Strength | | 25 mg | 50 mg | 25 mg | 50 mg |
| Active Agent | ASD formulation | 47.62 | 92 | 31.25 | 62.5 |
| Filler | Avicel ® PH 102 | 44.38 | — | 60.75 | 29.5 |
| | Lactose | — | — | — | — |

TABLE 5-continued

|  |  | Post-ASD Formulation | | | |
|---|---|---|---|---|---|
|  |  | 1 | 2 | 7 | 8 |
|  | monohydrate, Fast Flo ®, 316 |  |  |  |  |
| Disintegrant | Sodium Croscarmellose | 5 | 5 | 5 | 5 |
| Lubricant | Colloidal SiO$_2$ | 1 | 1 | 1 | 1 |
|  | Sodium Stearyl Fumarate | 2 | 2 | 2 | 2 |
|  | Total | 100 | 100 | 100 | 100 |
|  | Capsule Fill Weight, mg | 350 | 362 | 320 | 320 | a Active agent is 17.94% Compound A/5% TPGS/copovidone ASD powder
b Active agent is 29.90% Compound A/10% TPGS/HPMC ASD powder Table 6 presents examples of the disclosed formulations prepared by direct blending of the solid dispersion product with excipients and compressing the final blend into tablets. In particular, Table 6 presents the percentage of components by weight (w/w) of tablet formulations of 25 mg and 50 mg dosages of Compound A.

TABLE 6

|  |  | Post-ASD Formulation | | | | | | | |
|---|---|---|---|---|---|---|---|---|---|
|  | ASD Formulation Dose Strength | 3<br>a<br>25 mg | 4<br>a<br>50 mg | 5<br>a<br>50 mg | 6<br>a<br>50 mg | 9<br>b<br>25 mg | 10<br>b<br>50 mg | 11<br>b<br>50 mg | 12<br>b<br>50 mg |
| Active Agent | ASD formulation | 12.5 | 25 | 35 | 37 | 7.5 | 15 | 24.44 | 24.44 |
| Filler | Avicel ® PH 102 | 39.75 | 33.5 | 28.5 | 27.5 | 42.25 | 38.5 | 33.78 | 32.28 |
|  | Lactose monohydrate, Fast Flo ®, 316 | 39.75 | 33.5 | 28.5 | 27.5 | 42.25 | 38.5 | 33.78 | 32.28 |
| Disintegrant | Sodium Croscarmellose | 5 | 5 | 5 | 5 | 5 | 5 | 5 | 5 |
| Lubricant | Colloidal SiO$_2$ | 1 | 1 | 1 | 1 | 1 | 1 | 1 | 1 |
|  | Sodium Stearyl Fumarate | 2 | 2 | 2 | 2 | 2 | 2 | 2 | 2 |
| Filler | Hydroxypropyl cellulose | — | — | — | — | — | — | — | 3 |
| Total |  | 100 | 100 | 100 | 100 | 100 | 100 | 100 | 100 |
| Total Tablet Weight, mg |  | 1333 | 1333 | 952.38 | 900.88 | 1333 | 1333 | 818.33 | 818.33 | a Active agent is 17.94% Compound A/5% TPGS/copovidone ASD powder
b Active agent is 29.90% Compound A/10% TPGS/HPMC ASD powder Dual pH dissolution tests were performed to compare dissolution rates of various formulations using USP Apparatus II operating at 50 rpm. Dissolution medium was 500 mL 0.1 N HCl for the first 60 minutes followed by adding 400 mL 0.118 M phosphate buffer to make a final of 900 mL of 0.05 M phosphate buffer pH 6.8 for 75 minutes. Dissolution samples were assayed by HPLC.

Figure 3:
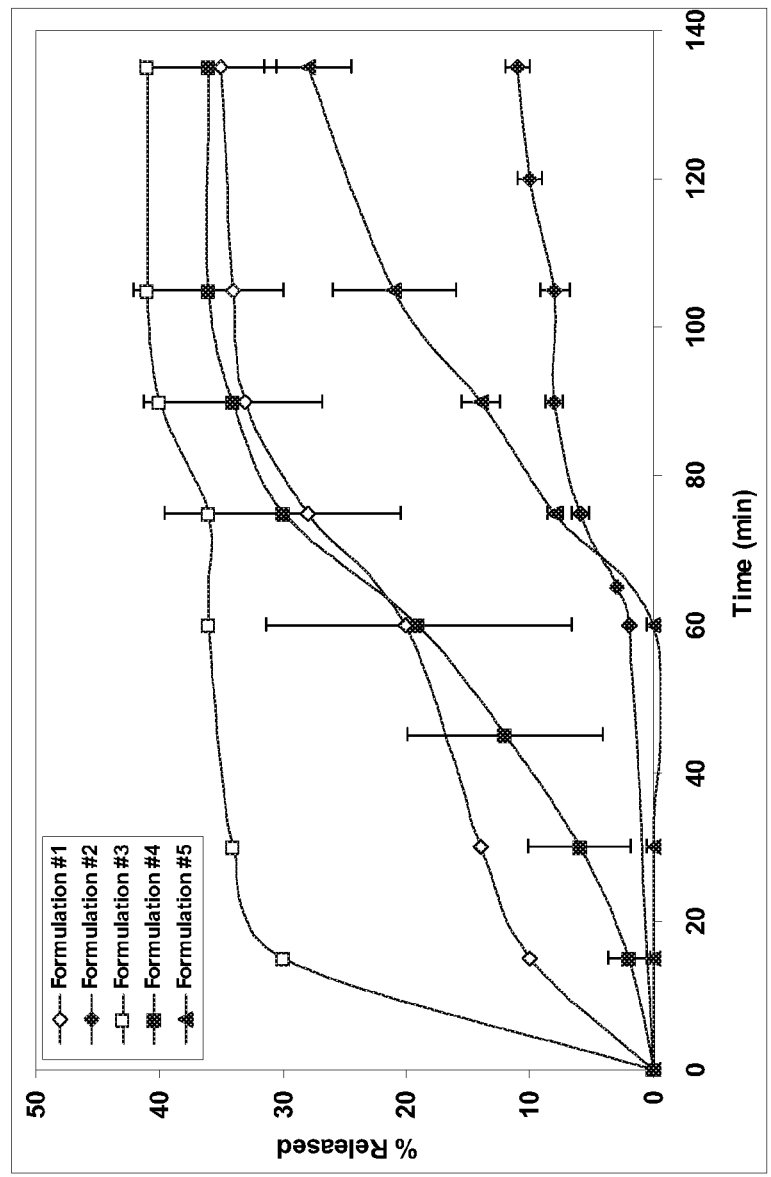
FIG. 3 is a graph illustrating in vitro release profiles of disclosed formulations at dual pH conditions.
Figure 4:
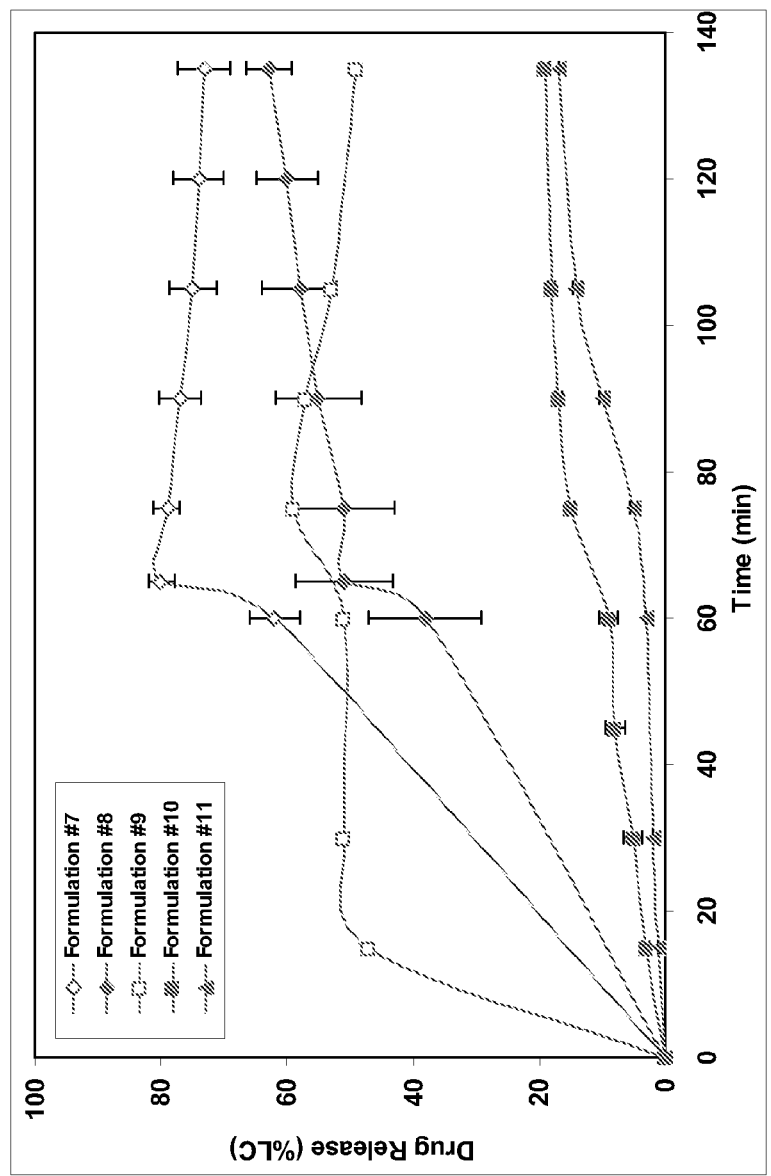
FIG. 4 is a graph illustrating in vitro release profiles of disclosed formulations at dual pH conditions.

Dissolution results for disclosed formulations 1-5 and 7-11 shown in Table 5 and in Table 6 are shown in FIG. 3 and FIG. 4, respectively. FIG. 3 shows in vitro release profiles of selected post-ASD formulations at dual pH conditions. The ASD powders in each of the post-ASD formulations include 17.94% Compound A, 5% TPGS and copovidone. FIG. 4 shows in vitro release profiles of selected post-amorphous solid dispersion (ASD) formulations at dual pH conditions. The ASD powders in each of the post-ASD formulations include 29.90% Compound A/10% TPGS/HPMC amorphous solid dispersion. The results show that dissolution rate and extent of drug released of amorphous solid dispersion-based formulations is desirable.

b. Roller Compaction

In embodiments, the solid dispersion product undergoes roller compaction. Roller compaction includes the steps of blending the solid dispersion product with one or more disintegrants, lubricants and combinations thereof; feeding the blend into a roller compactor to densify loose powder into ribbons; milling the resultant ribbons into granules; and blending the granules with extra-granular excipients.

Intragranular excipients may include one or more of polymers, stabilizing agents, fillers, alkalizing agents, surfactants, and any other suitable intragranular excipients and combinations thereof.

Disintegrants may include, for example, cross-linked sodium carboxymethylcellulose, such as sodium croscarmellose or any other suitable disintegrant in any suitable amounts including, for example, from about 2% to about 35% w/w or from about 3% to about 30% of the pharmaceutical product. In embodiments, extragranular excipients include about 3% disintegrant. In embodiments, extragranular excipients include about 5% disintegrant. In embodiments, extragranular excipients include about 15% disintegrant. In embodiments, extragranular excipients include about 30% disintegrant.

Lubricants may include, for example, sodium stearyl fumarate, colloidal silicon dioxide or any other suitable lubricant in any suitable amounts including, for example, from about 0.1% to about 15% w/w or from about 0.5% to about 10% of the pharmaceutical product. In embodiments, extragranular excipients include about 0.5% lubricant. In embodiments, extragranular excipients include about 1% lubricant. In embodiments, extragranular excipients include about 5% lubricant. In embodiments, extragranular excipients include about 10% lubricant.

Extragranular excipients may include one or more of fillers, alkalizing agents, disintegrants and lubricants, and any other suitable extragranular excipients and combinations thereof.

Fillers may include, for example, microcrystalline cellulose, such as Avicel® PH102, lactose monohydrate and other suitable fillers. At least about 5% to about 25% w/w or from about 10% to about 23% w/w of the pharmaceutical product may be filler. In embodiments, extragranular excipients include about 10% filler. In embodiments, extragranular excipients include about 11% filler. In embodiments, extragranular excipients include about 15% filler. In embodiments, extragranular excipients include about 18% filler. In embodiments, extragranular excipients include about 23% filler.

Disintegrants may include, for example, cross-linked sodium carboxymethylcellulose, such as sodium croscarmellose or any other suitable disintegrant in any suitable amounts including, for example, from about 1% to about 25% w/w or from about 2% to about 20% of the pharmaceutical product. In embodiments, extragranular excipients include about 2% disintegrant. In embodiments, extragranular excipients include about 5% disintegrant. In embodiments, extragranular excipients include about 10% disintegrant. In embodiments, extragranular excipients include about 20% disintegrant.

Lubricants may include, for example, sodium stearyl fumarate, colloidal silicon dioxide or any other suitable lubricant in any suitable amounts including, for example, from about 0.1% to about 15% w/w or from about 0.5% to about 10% of the pharmaceutical product. In embodiments, extragranular excipients include about 0.5% lubricant. In embodiments, extragranular excipients include about 1% lubricant. In embodiments, extragranular excipients include about 5% lubricant. In embodiments, extragranular excipients include about 10% lubricant.

The final blend may be compressed into tablets or encapsulated into capsules. In embodiments, the final blend is compressed into tablets using a rotary press, hydraulic press, such as a Carver press, or any other suitable compression mechanism. At least one additive selected from flow regulators, disintegrants, bulking agents and lubricants is preferably used in compacting the granules. Disintegrants promote a rapid disintegration of the compact in the stomach and keep the liberated granules separate from one another. Suitable disintegrants are crosslinked polymers such as crosslinked polyvinyl pyrrolidone and crosslinked sodium carboxymethyl cellulose. Suitable bulking agents are selected from lactose, calcium hydrogen phosphate, microcrystalline cellulose (Avicel®), magnesium oxide, natural or pre-gelatinized potato or corn starch, polyvinyl alcohol.

Suitable flow regulators are selected from highly dispersed silica (Aerosil®), and animal or vegetable fats or waxes.

A lubricant is preferably used in compacting the granules. Suitable lubricants are selected from polyethylene glycol (e.g., having a Mw of from 1000 to 6000), magnesium and calcium stearates, sodium stearyl fumarate, talc, and the like.

Various other additives may be used, for example dyes such as azo dyes, organic or inorganic pigments such as aluminum oxide or titanium dioxide, or dyes of natural origin; stabilizers such as antioxidants, light stabilizers, radical scavengers, or stabilizers against microbial attack.

Tablets may be coated with a suitable coating including enteric coating. In order to facilitate the intake of such a dosage form by a mammal, it is advantageous to give the dosage form an appropriate shape. Large tablets that can be swallowed comfortably are therefore preferably elongated rather than round in shape. A film coat on the tablet further contributes to the ease with which it can be swallowed. A film coat also improves taste and provides an elegant appearance. If desired, the film coat may be an enteric coat. The film coat usually includes a polymeric film-forming material such as (hydroxypropyl)methyl cellulose, hydroxypropyl cellulose, and acrylate or methacrylate copolymers. Besides a film-forming polymer, the film coat may further comprise a plasticizer, e.g. polyethylene glycol, a surfactant, e.g. a Tween® type, and optionally a pigment, e.g. titanium dioxide or iron oxides. The film-coating may also comprise talc as an anti-adhesive. The film coat usually accounts for less than about 5% by weight of the dosage form.

Table 7 presents further examples of the disclosed formulations prepared by roller compaction of the active agent with excipients and compressing the final blend into tablets. In particular, Table 7 presents the percentage of components by weight (w/w) of tablet formulations of 50 mg and 100 mg dosages of Compound A. The purpose of developing formulations 13 and 14 is to achieve higher dose strength per tablet while keeping similar drug release as post-ASD formulation 5—see Table 6, a reference formulation, which has a lower dose strength per tablet. The advantage achieved with formulations such as formulations 13 and 14 is increased patient compliance, as fewer tablets need to be administered. About 70 percent of the pharmaceutical product is active agent.

TABLE 7

| | | Post-ASD Formulation | | | |
|---|---|---|---|---|---|
| | | 13 | | 14 | |
| | | ASD Formulation | | | |
| | | a | | a | |
| | | Dose strength | | | |
| | | 50 mg | | 100 mg | |
| | Component | Amount per tablet (mg) | % w/w | Amount per tablet (mg) | % w/w |
| | Intra-granular | | | | |
| Active Agent | ASD formulation | 333.33 | 70.00 | 666.66 | 67.99 |
| Disintegrant | Sodium croscarmellose | 14.29 | 3.00 | 28.58 | 2.91 |
| Lubricant | Colloidal silicon dioxide | 2.38 | 0.50 | 4.76 | 0.49 |
| | Sodium stearyl fumerate | 4.76 | 1.00 | 9.52 | 0.97 |
| | Extra-granular | | | | |
| Filler | Microcrystalline Cellulose (Avicel ® PH 102) | 52.38 | 11.00 | 104.76 | 10.67 |
| | Lactose Monohydrate, Fast Flo ® (#316) | 52.38 | 11.00 | 104.76 | 10.67 |
| Disintegrant | Croscarmellose, Sodium | 9.52 | 2.00 | 19.04 | 1.94 |
| Lubricant | Colloidal Silicon Dioxide | 2.38 | 0.50 | 4.76 | 0.48 |
| | Sodium Stearyl Fumarate | 4.76 | 1.00 | 9.52 | 0.97 |
| Coating | Opadry ® II yellow | — | — | 28.57 | 2.91 |
| | Total Tablet Weight (mg)/Percentage (w/w) | 476.18 | 100 | 980.97 | 100 | a Active agent is 17.94% Compound A/5% TPGS/copovidone ASD powder

In Vitro Dissolution Testing

Bi-phasic dissolution tests were performed to compare various formulations. The USP apparatus IV flow cell system was used for sample preparation. Tablets were first exposed to 10 mL of 0.01 N HCl at 37° C. and 150 rpm for 30 minutes. The dissolution bath was a standard USP apparatus II with dual paddles (adjustable secondary paddle was added for the organic phase) set at 50 rpm. Dissolution medium was 40 mL pH 6.8 phosphate buffer (bottom) and 30 mL octanol (top) maintained at 37° C. Cole-Parmer pumps were used to circulate the aqueous buffer phase between the dissolution vessel and flow cell. The flow rate of the aqueous phase into flow cell is 5 mL/minute. Drug dissolved in the aqueous buffer phase and partitioned into the organic octanol phase. Micro-Diss (PION) dip UV probes were used to measure the UV absorption of drug at 312 nm in the octanol phase in situ. Sampling was performed every 2 minutes over a 90 minute period.

Bi-phasic dissolution results as shown in FIG. 11 indicate that drug release from Formulations 13 and 14 are comparable with that from the reference tablet formulation prepared by direct blending of the solid dispersion product containing a 50 mg dose of Compound A (post-ASD formulation 5—see Table 6).

In Vivo Bioavailability Study in Dog Model

In vivo bioavailability studies of roller compaction formulations 13 and 14 were conducted in groups of four dogs. Each dog received a 50 or 100 mg oral dose of each formulation. The dogs were fasted overnight prior to dosing with food provided four hours after drug administration. Each dog received a subcutaneous dose of histamine ~30 minutes prior to dosing. The plasma concentrations of Compound A were determined by HPLC-MS/MS at the completion of all dosing periods.

Table 8 presents a summary of pharmacokinetics data following oral administration of formulations 13 and 14 in the dog model. The pharmacokinetics data demonstrate that both formulations 13 and 14 achieved equivalent exposure compared to the reference formulation as reflected by the similar mean areas under the plasma concentration curves (AUC) normalized by dose strength.

TABLE 8

| Formulation | Dose (mg) | $t_{1/2}$ | $C_{max}$ | $T_{max}$ | AUC | AUC/D |
| --- | --- | --- | --- | --- | --- | --- |
| Reference | 50 | 9.2° | 5.33 | 2.6 | 73.4 | 13.49 |
| 13 | 50 | 9.6° | 5.47 | 3.5 | 75.17 | 12.45 |
| 14 | 100 | 7.9° | 9.18 | 2.3 | 135.16 | 11.93 |

In Vivo Bioavailability Study in Human

In vivo bioavailability was assessed in an open-label, two-period, randomized, non-fasting, complete-crossover study in 16 healthy subjects to evaluate the relative bioavailability of a high drug load tablet formulation of Compound A (Formulation 13) compared to a reference tablet formulation prepared by direct blending of the solid dispersion product containing a 50 mg dose of Compound A (post-ASD formulation 5—see Table 6). Each subject received single doses of 100 mg Compound A administered as the high drug load tablet (2×50 mg tablets) and reference tablet (2×50 mg tablets).

Human pharmacokinetics study results are shown in Table 9. The AUC values met equivalence criteria though the mean AUC value of the high drug load tablet was approximately 10% lower compared to the reference tablet. The high drug load tablet exhibited a later $T_{max}$ (~4.4 hours) compared to the reference tablet (3.2 hours). The mean $t_{1/2}$ was consistent across formulations, ranging from 8 to 9 hours. The variability in $C_{max}$ and AUC observed following administration of the disclosed formulations was comparable across all formulations, ranging from 37 to 53%.

TABLE 9

| Parameter | Reference Tablet N = 16 | High Drug Load Tablet N = 16 |
| --- | --- | --- |
| $C_{max}$ (ng/mL) | 392 (37) | 320 (43) |
| $T_{max}$ (hr) | 3.2 (33) | 4.4 (40) |
| $AUC_t$ (ng * hr/mL) | 3452 (53) | 3058 (39) |
| $AUC_\infty$ (ng * hr/mL) | 3470 (53) | 3074 (39) |
| $t_{1/2}$ (hr)# | 8.0 (20) | 8.7 (24) | harmonic mean

Wet Granulation

Alternatively, the disclosure provides pharmaceutical products, compositions and formulations comprising a phenyl uracil compound, such as Compound A, at least one alkalizing agent having a pKa value greater than the pKa of the phenyl uracil compound; at least one water-soluble low molecular weight polymer to inhibit crystallization growth, and at least one surfactant. The pharmaceutical products may be formulated by processes such as milling, wet granulation and combinations thereof. In embodiments, a wet granulation process is used to mix Compound A, the alkalizing agent, the polymer and the surfactant to foster intimate interaction between the components of the formulation.

The composition may be obtained by a process, wherein the process includes at least one of maintaining high pH in the diffusion layer by adding at least one alkalizing agent having a pKa value greater than the pKa of the phenyl uracil compound; 2) using a water soluble low molecular weight polymer to inhibit crystallization growth; 3) increasing the concentration of the drug in the diffusion layer; 4) increasing wettability of the drug/formulation by mixing surfactants; 4) increasing API surface area by reducing particle size; 5) using a wet granulation process to mix the drug with excipients to foster intimate interaction, and combinations thereof.

The disclosure provides methods for preparing a pharmaceutical product comprising a phenyl uracil compound, such as Compound A, wherein the method comprises at least one of maintaining high pH in the diffusion layer; inhibiting crystallization growth; increasing the concentration of the phenyl uracil compound in the diffusion layer; increasing wettability of the phenyl uracil compound; and reducing particle size of the phenyl uracil compound.

In embodiments, the disclosure provides methods of preparing a pharmaceutical composition comprising a phenyl uracil compound. The method includes combining into a mixture a phenyl uracil compound, such as Compound A, with at least one alkalizing agents having pKa values greater than the pKa of the phenyl uracil compound, at least one water soluble low molecular weight polymer and at least one surfactant; and combining the mixture with at least one pharmaceutically acceptable excipient.

In embodiments, the phenyl uracil compound undergoes fluid bed or high shear wet granulation together with a granulation fluid and an alkalizing agent and intragranular excipients. The resultant granules may be combined with extragranular excipients before being compressed into tablets or encapsulated into capsules.

Figure 5:
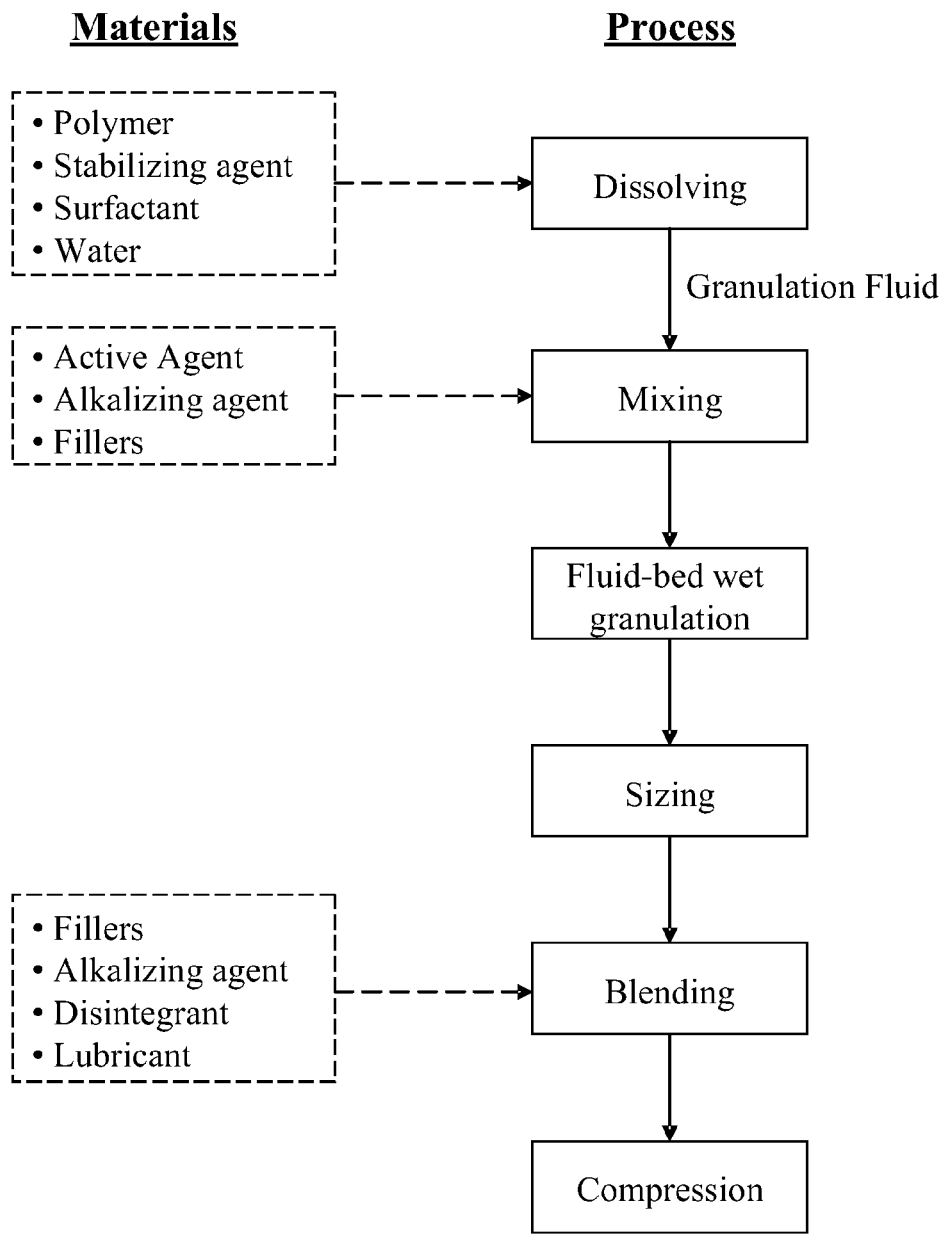
FIG. 5 is a flow diagram illustrating a manufacturing process for tablets.

As illustrated in FIG. 5, a wet granulation process (process I) may include the following steps: dissolving a polymer, stabilizing agent, surfactant and water to form a granulation fluid; mixing the active agent, alkalizing agent and fillers with the granulation fluid; granulating the mixture by fluid-bed wet granulation; sizing the resultant granules; blending the granules with one or more fillers, alkalizing agents, disintegrants, and lubricants; and compressing the resultant mixture into tablets.

The granulation fluid may include a solution of one or more polymers, stabilizing agents, surfactants, solvents, such as water, or combinations thereof.

Polymers may include, for example, copovidone, polyvinylpyrrolidone, such as PVP K30, (hydroxypropyl)methylcellulose, such as HPMC-E5, HPMC-AS, HPMC-P55, and other suitable polymers. At least about 0% to about 10% w/w or from about 4% to about 8% w/w of the pharmaceutical product may be polymer. In embodiments, intragranular excipients include no polymer. In embodiments, intragranular excipients include about 4% polymer. In embodiments, intragranular excipients include about 8% polymer.

Surfactants may include, for example, vitamin E d-alpha tocopheryl polyethylene glycol succinate (Vit E TPGS) and other suitable surfactants. At least about 5% to about 15% w/w or from about 6% to about 12% w/w of the pharmaceutical product may be a stabilizing agent. In embodiments, intragranular excipients include about 6% stabilizing agent. In embodiments, intragranular excipients include about 12% stabilizing agent.

Fillers may include, for example, microcrystalline cellulose, such as Avicel® PH102, lactose monohydrate and other suitable fillers. At least about 15% to about 40% w/w or from about 20% to about 30% w/w of the pharmaceutical product may be filler. In embodiments, intragranular excipients include about 20% filler. In embodiments, intragranular excipients include about 24% filler. In embodiments, intragranular excipients include about 26% filler. In embodiments, intragranular excipients include about 30% filler. In embodiments, intragranular excipients include about 38% filler.

The filler of the pharmaceutical product may include a combination of fillers such as a combination of microcrystalline cellulose and lactose monohydrate. At least about 15% to about 25% w/w or from about 15% to about 20% w/w of the pharmaceutical product may be microcrystalline cellulose, and at least about 5% to about 20% w/w or from about 8% to about 10% w/w of the pharmaceutical product may be lactose monohydrate. In embodiments, intragranular excipients include about 20% microcrystalline cellulose and about 10% lactose monohydrate. In embodiments, intragranular excipients include about 23% microcrystalline cellulose and about 16% lactose monohydrate. In embodiments, intragranular excipients include about 20% microcrystalline cellulose and about 10% lactose monohydrate. In embodiments, intragranular excipients include about 18% microcrystalline cellulose and about 9% lactose monohydrate. In embodiments, intragranular excipients include about 17% microcrystalline cellulose and about 9% lactose monohydrate. In embodiments, intragranular excipients include about 16% microcrystalline cellulose and about 8% lactose monohydrate.

Alkalizing agents may include, for example, sodium carbonate, sodium bicarbonate, sodium arginine or any other suitable alkalizing agent in any suitable amounts including, for example, from about 2% to about 15% w/w or from about 5% to about 10% of the pharmaceutical product.

Surfactants may include, for example, polaxamers, such as Lutrol® F127, ethylene oxide/propylene oxide block copolymers, such as Pluronic® F68, sodium dodecyl sulphate or any other suitable surfactant. At least about 2% to about 5% w/w of the pharmaceutical product may be surfactant. In embodiments, intragranular excipients include about 3% surfactant.

Disintegrants may include, for example, cross-linked sodium carboxymethylcellulose, such as sodium croscarmellose or any other suitable disintegrant in any suitable amounts including, for example, from about 2% to about 35% w/w or from about 3% to about 30% of the pharmaceutical product. In embodiments, extragranular excipients include about 3% disintegrant. In embodiments, extragranular excipients include about 5% disintegrant. In embodiments, extragranular excipients include about 15% disintegrant. In embodiments, extragranular excipients include about 30% disintegrant.

Lubricants may include, for example, sodium stearyl fumarate, colloidal silicon dioxide or any other suitable lubricant in any suitable amounts including, for example, from about 0.1% to about 15% w/w or from about 0.5% to about 10% of the pharmaceutical product. In embodiments, extragranular excipients include about 0.5% lubricant. In embodiments, extragranular excipients include about 2% lubricant. In embodiments, extragranular excipients include about 5% lubricant. In embodiments, extragranular excipients include about 10% lubricant.

Solvents may include aqueous and non-aqueous solvents. In embodiments the solvent is water in sufficient quantity.

Extragranular excipients may include one or more of fillers, alkalizing agents, disintegrants and lubricants, and any other suitable extragranular excipients and combinations thereof.

Fillers may include, for example, microcrystalline cellulose, such as Avicel® PH102, lactose monohydrate and other suitable fillers. At least about 5% to about 25% w/w or from about 10% to about 23% w/w of the pharmaceutical product may be filler. In embodiments, extragranular excipients include about 10% filler. In embodiments, extragranular excipients include about 13% filler. In embodiments, extragranular excipients include about 15% filler. In embodiments, extragranular excipients include about 18% filler. In embodiments, extragranular excipients include about 23% filler.

Alkalizing agents may include, for example, sodium carbonate, sodium bicarbonate, sodium arginine or any other suitable alkalizing agent in any suitable amounts including, for example, from about 2% to about 15% w/w or from about 5% to about 10% of the pharmaceutical product. In embodiments, extragranular excipients include about 5% alkalizing agent. In embodiments, extragranular excipients include about 10% alkalizing agent.

Disintegrants may include, for example, cross-linked sodium carboxymethylcellulose, such as sodium croscarmellose or any other suitable disintegrant in any suitable amounts including, for example, from about 1% to about 25% w/w or from about 2% to about 20% of the pharmaceutical product. In embodiments, extragranular excipients include about 2% disintegrant. In embodiments, extragranular excipients include about 5% disintegrant. In embodiments, extragranular excipients include about 10% disintegrant. In embodiments, extragranular excipients include about 20% disintegrant.

Lubricants may include, for example, sodium stearyl fumarate, colloidal silicon dioxide or any other suitable lubricant in any suitable amounts including, for example, from about 0.1% to about 15% w/w or from about 0.5% to about 10% of the pharmaceutical product. In embodiments, extragranular excipients include about 0.5% lubricant. In embodiments, extragranular excipients include about 2% lubricant. In embodiments, extragranular excipients include about 5% lubricant. In embodiments, extragranular excipients include about 10% lubricant.

The final blend may be compressed into tablets or encapsulated into capsules. In embodiments, the final blend is compressed into tablets using a rotary press, hydraulic press, such as a Carver press, or any other suitable compression mechanism. At least one additive selected from flow regulators, disintegrants, bulking agents and lubricants is preferably used in compacting the granules. Disintegrants promote a rapid disintegration of the compact in the stomach and keep the liberated granules separate from one another. Suitable disintegrants are crosslinked polymers such as crosslinked polyvinyl pyrrolidone and crosslinked sodium carboxymethyl cellulose. Suitable bulking agents are selected from lactose, calcium hydrogen phosphate, microcrystalline cellulose (Avicel®), magnesium oxide, natural or pre-gelatinized potato or corn starch, polyvinyl alcohol.

Suitable flow regulators are selected from highly dispersed silica (Aerosil®), and animal or vegetable fats or waxes.

A lubricant is preferably used in compacting the granules. Suitable lubricants are selected from polyethylene glycol (e.g., having a Mw of from 1000 to 6000), magnesium and calcium stearates, sodium stearyl fumarate, talc, and the like.

Various other additives may be used, for example dyes such as azo dyes, organic or inorganic pigments such as aluminum oxide or titanium dioxide, or dyes of natural origin; stabilizers such as antioxidants, light stabilizers, radical scavengers, or stabilizers against microbial attack.

Tablets may be coated with a suitable coating including an enteric coating. In order to facilitate the intake of such a dosage form by a mammal, it is advantageous to give the dosage form an appropriate shape. Large tablets that can be swallowed comfortably are therefore preferably elongated rather than round in shape. A film coat on the tablet further contributes to the ease with which it can be swallowed. A film coat also improves taste and provides an elegant appearance. If desired, the film coat may be an enteric coat. The film coat usually includes a polymeric film-forming material such as (hydroxypropyl)methyl cellulose, hydroxypropyl cellulose, and acrylate or methacrylate copolymers. Besides a film-forming polymer, the film coat may further comprise a plasticizer, e.g. polyethylene glycol, a surfactant, e.g. a Tween® type, and optionally a pigment, e.g. titanium dioxide or iron oxides. The film-coating may also comprise talc as anti-adhesive. The film coat usually accounts for less than about 5% by weight of the dosage form.

Table 10 presents further examples of the disclosed formulations prepared by wet granulation of the active agent with excipients and compressing the final blend into tablets. In particular, Table 10 presents the percentage of components by weight (w/w) of formulations of 100 mg dosages of Compound A in tablet dosage forms that contain stabilizing agent and polymer.

TABLE 10

| | | Formulation | | |
|---|---|---|---|---|
| | | 9 | 10 | 11 |
| Intra-granular | | | | |
| Active Agent | Compound A | 26.6 | 26.6 | 26.6 |
| Polymer | Copovidone K28 | 8 | 8 | 8 |
| Surfactant | Vitamin E TPGS | 12 | 12 | 12 |
| Filler | Avicel ® PH 101 | 21.1 | 18.4 | 15.8 |
| | Lactose monohydrate | 10.5 | 9.2 | 7.8 |
| Solvent | Water | q.s. | q.s. | q.s. |
| Extra-granular | | | | |
| Filler | Avicel ® PH 102 | 22.8 | 22.8 | 22.8 |
| Disintegrant | Na Croscarmellose | 5 | 5 | 5 |
| Lubricant | Sodium Stearyl Fumarate | 2 | 2 | 2 |
| | Total | 100 | 100 | 100 |

Table 11 presents further examples of the disclosed formulations prepared by wet granulation of the active agent with excipients and compressing the final blend into tablets. In particular, Table 11 presents the percentage of components by weight (w/w) of formulations of 100 mg dosages of Compound A in tablet dosage forms that contain stabilizing agent, polymer and alkalizing agent.

TABLE 11

| | | Formulation | | | | | |
|---|---|---|---|---|---|---|---|
| | Component | 1 % w/w | 3 % w/w | 5 % w/w | 6 % w/w | 7 % w/w | 13 % w/w |
| Intra-granular | | | | | | | |
| Active Agent | Compound A | 26.6 | 26.6 | 26.6 | 26.6 | 28.6 | 26.6 |
| Polymer | Copovidone K28 | 8 | 8 | 8 | 8 | 8 | 8 |
| Surfactant | Vitamin E TPGS | 12 | 12 | 12 | 12 | 12 | 12 |
| Filler | Avicel ® PH 101 | 20.6 | 20.6 | 15.8 | 15.8 | 15.8 | 15.8 |
| | Lactose monohydrate | 10.4 | 10.4 | 7.8 | 7.8 | 7.8 | 7.8 |
| Alkalizing Agent | Sodium Carbonate | — | — | — | 10 | | — |
| | Sodium Arginine | — | — | — | — | | 5 |
| Solvent | Water | q.s. | q.s. | q.s. | q.s. | q.s | q.s. |
| Extra-granular | | | | | | | |
| Filler | Avicel ® PH 102 | 10.4 | 15.4 | 12.8 | 12.8 | 12.8 | 17.8 |
| Alkalizing Agent | Sodium Carbonate | 5 | — | 10 | — | — | — |
| Disintegrant | Na Croscarmellose | 5 | 5 | 5 | 5 | 5 | 5 |
| Lubricant | Sodium Stearyl Fumarate | 2 | 2 | 2 | 2 | 2 | 2 |
| Total | | 100 | 100 | 100 | 100 | 100 | 100 |

Table 12 presents further examples of the disclosed formulations prepared by wet granulation of the active agent with excipients and compressing the final blend into tablets and coating the tablets with an enteric coating. In particular, Table 12 presents the percentage of components by weight (w/w) of formulations of 100 mg dosages of Compound A in an enteric coated tablet dosage form that contains the stabilizing agent, polymer and alkalizing agent.

TABLE 12

|  | Component | Formulation 2 % w/w | Formulation 4 % w/w |
|---|---|---|---|
| Intra-granular | | | |
| Active Agent | Compound A | 26.6 | 26.6 |
| Polymer | Copovidone K28 | 8 | 8 |
| Surfactant | Vitamin E TPGS | 12 | 12 |
| Filler | Avicel ® PH 101 | 20.6 | 20.6 |
|  | Lactose monohydrate | 10.4 | 10.4 |
|  | Water | q.s. | q.s. |
| Extra-granular | | | |
| Filler | Avicel ® PH 102 | 10.4 | 15.4 |
| Alkalizing Agent | Sodium Carbonate | 5 | — |
|  | Sodium Bicarbonate | — | — |
| Disintegrant | Na Croscarmellose | 5 | 5 |
| Lubricant | Sodium Stearyl Fumarate | 2 | 2 |
|  | Total | 100 | 100 |

Table 13 presents further examples of the disclosed formulations prepared by wet granulation of the active agent with excipients and compressing the final blend into tablets. In particular, Table 13 presents the percentage of components by weight (w/w) of formulations of 100 mg dosages of Compound A in tablet dosage forms that contain stabilizing agent, polymer, alkalizing agent and surfactant.

TABLE 13

|  | Component | Formulation 15 % w/w | Formulation 16 % w/w | Formulation 17 % w/w |
|---|---|---|---|---|
| Intra-granular | | | | |
| Active Agent | Compound A | 26.6 | 26.6 | 26.6 |
| Polymer | Copovidone K28 | 8 | 8 | 8 |
| Surfactant | Vitamin E TPGS | 12 | 12 | 12 |
| Filler | Avicel ® PH 101 | 16.8 | 16.8 | 16.8 |
|  | Lactose monohydrate | 8.8 | 8.8 | 8.8 |
| Alkalizing Agent | Sodium Carbonate | 5 | 5 | 5 |
| Surfactant | Lutrol ® F127 | 3 | — | — |
|  | Pluronic ® F68 | — | 3 | — |
|  | Sodium dodecyl sulfate | — | — | 3 |
| Solvent | Water | q.s. | q.s. | q.s. |
| Extra-granular | | | | |
| Filler | Avicel ® PH 102 | 12.8 | 12.8 | 12.8 |
| Disintegrant | Na Croscarmellose | 5 | 5 | 5 |
| Lubricant | Sodium Stearyl Fumarate 33 | 2 | 2 | 2 |
|  | Total | 100 | 100 | 100 |

In Vitro Dissolution Test

Dual pH dissolution tests were performed to compare dissolution rates of various formulations using USP Apparatus II operating at 50 rpm. Dissolution medium was 500 mL 0.1 N HCl for first 60 minutes followed by adding 400 mL 0.118 M phosphate buffer to make a final of 900 mL of 0.05 M phosphate buffer pH 6.8 for 75 minutes. Dissolution samples were assayed by HPLC. A formulation prepared by direct blending and compression of Compound A with Avicel® PH102, lactose monohydrate, sodium croscarmellose and sodium stearyl fumarate was used as a control. The results are provided in FIGS. 7-9.

Figure 7:
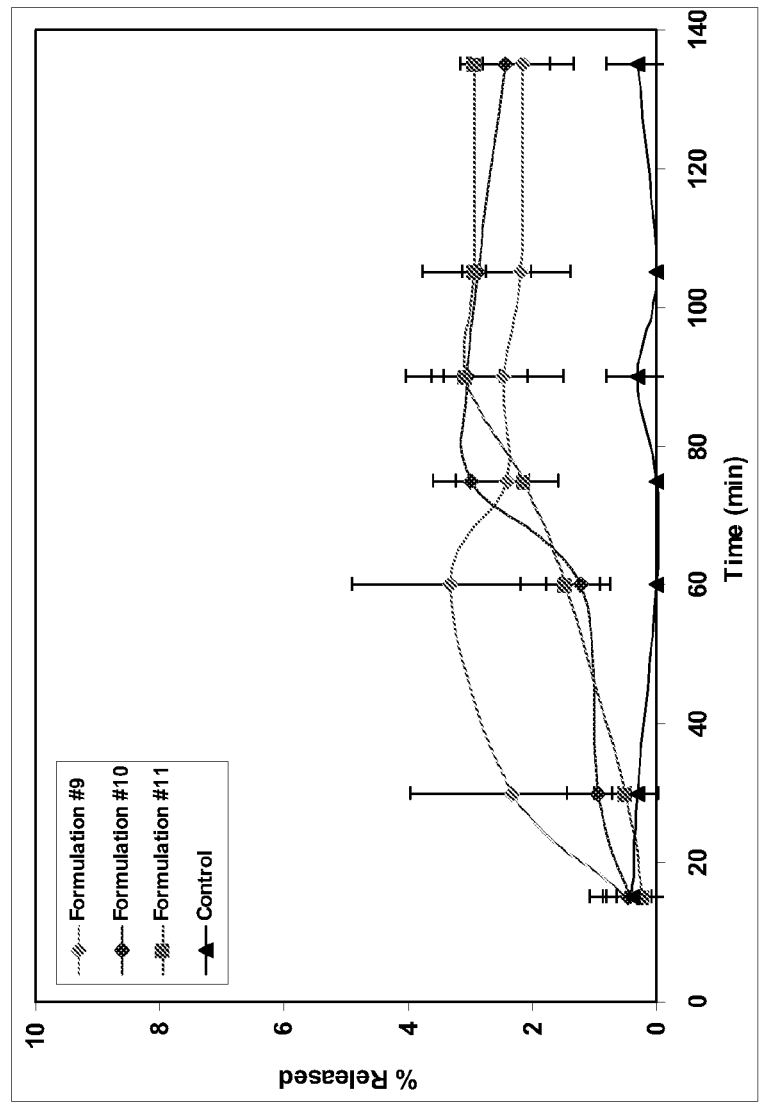
FIG. 7 is a graph illustrating in vitro release profiles of formulations containing the stabilizing agent and polymer.
Figure 8:
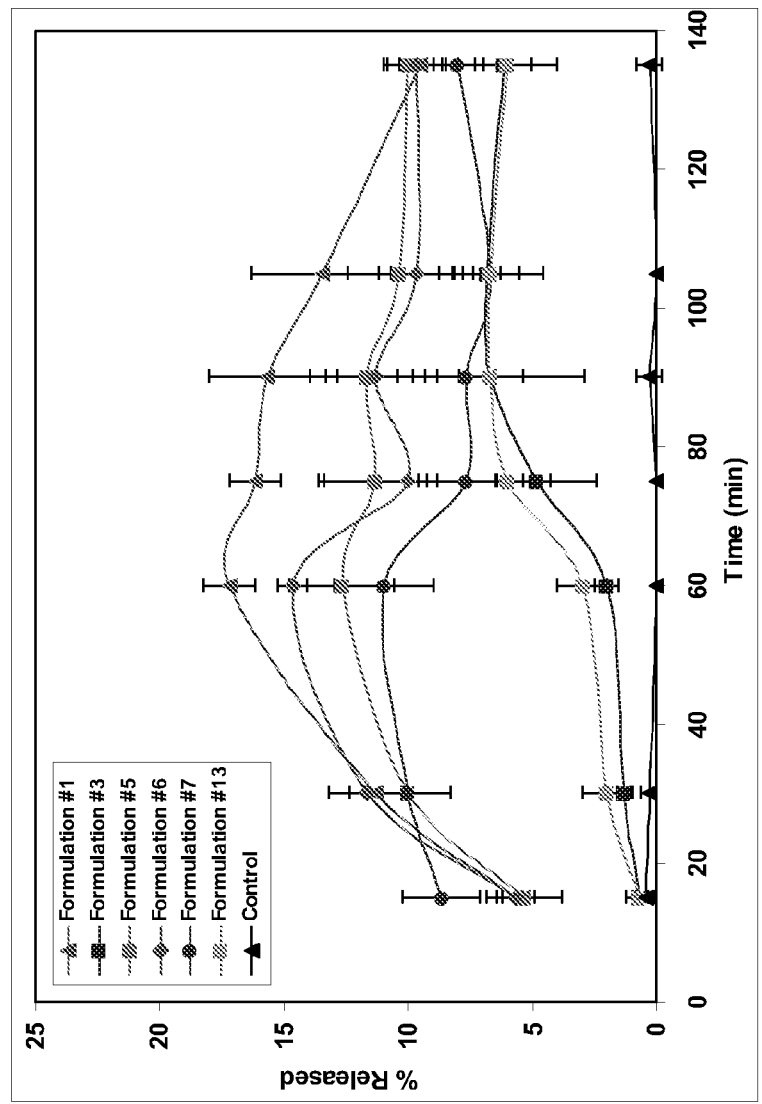
FIG. 8 is a graph illustrating in vitro release profiles of formulations containing the stabilizing agent, polymer and alkalizing agent.
Figure 9:
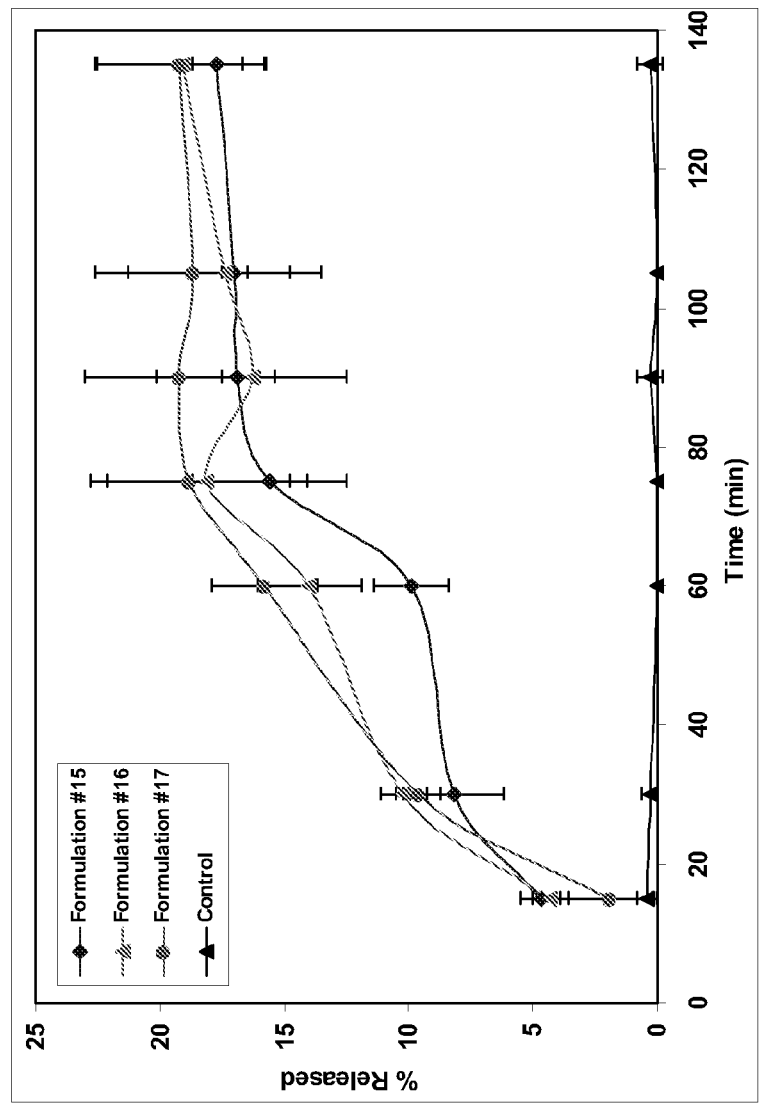
FIG. 9 is a graph illustrating in vitro release profiles of formulations containing the stabilizing agent, polymer, alkalizing agent and surfactant.

In vitro drug release profiles of the tablet formulations containing the stabilizing agent and polymer are shown in FIG. 7. In vitro drug release profiles of the tablet formulations containing the stabilizing agent, polymer and alkalizing agent are shown in FIG. 8. In vitro drug release profiles of the tablet formulations containing the stabilizing agent, polymer, alkalizing agent and surfactant are shown in FIG. 9. The results demonstrate that dissolution rate and extent of drug released from all invented formulations are higher than those of the control formulation.

In Vivo Bioavailability Study in Dog Model

In vivo bioavailability of selected invented formulations and the control formulation was assessed in a study using a lipid-based formulation as a reference. All formulations were dosed at a strength of 100 mg/animal in fasted dogs.

Results of the bioavailability study are summarized in Table 14. It was demonstrated that the disclosed formulations have higher exposure than the control formulation and comparable exposure as the reference formulation as reflected by the mean areas under the plasma concentration curves (AUC).

TABLE 14

| Formulation | $t_{1/2}$ | AUC | $C_{max}$ | $T_{max}$ |
|---|---|---|---|---|
| Control | 5.5° | 10.83 (8.79) | 1.11 (0.88) | 3.1 (0.6) |
| Reference | 8.7° | 59.82 (4.87) | 4.37 (0.37) | N/A |
| #1 | 7.3° | 68.45 (17.89) | 6.29 (1.29) | 2.8 (1.1) |
| #2 | 7.1° | 53.21 (8.54) | 4.37 (0.48) | 4.5 (0.5) |
| #3 | 8.0° | 46.12 (11.29) | 4.31 (0.76) | 1.4 (0.1) |

°harmonic mean;
AUC [μg · hr/mL]

Milled/Wet-Granulation

In embodiments, the active agent is milled in an aqueous suspension with an alkaline agent and excipients. In such embodiments, the aqueous suspension is coated on the other excipients and the coated excipients undergo a wet granulation process such as the process described above.

Figure 6:
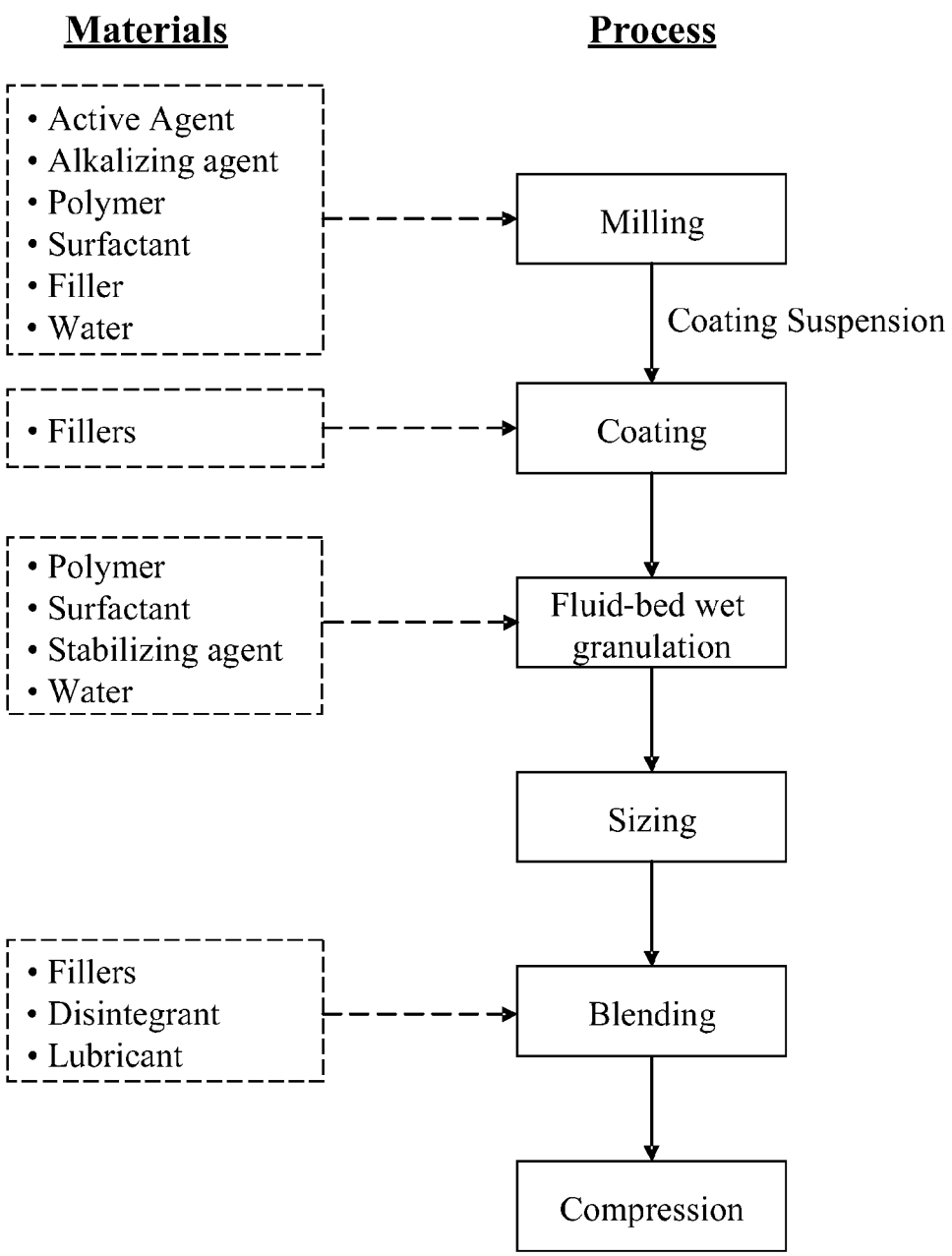
FIG. 6 is a flow diagram illustrating a manufacturing process for tablets.

As illustrated in FIG. 6 (process II), milling and wet granulation may be combined to prepare the intra-granular portion of the formulation. Such embodiments may include the following steps: milling the active agent together with one or more alkalizing agents, polymers, surfactants, fillers and solvents such as water; coating one or more fillers with the coating suspension; dissolving one or more polymers, stabilizing agents, surfactants and solvents, such as water, to form a granulation fluid; mixing the coated filler, alkalizing agent and fillers with the granulation fluid; granulating the mixture by fluid-bed wet granulation; sizing the resultant granules; blending the granulation with one or more fillers, disintegrants, and lubricants; and compressing the resultant mixture into tablets.

Polymers may include, for example, copovidone, polyvinylpyrrolidone, such as PVP K30, (hydroxypropyl)methyl cellulose, such as HPMC-E5, HPMC-AS, HPMC-P55, and other suitable polymers. At least about 0% to about 10% w/w or from about 4% to about 8% w/w of the pharmaceutical product may be polymer. In embodiments, intragranular excipients include no polymer. In embodiments, intragranular excipients include about 4% polymer. In embodiments, intragranular excipients include about 8% polymer.

Surfactants may include, for example, vitamin E d-alpha tocopheryl polyethylene glycol succinate (Vit E TPGS) and other suitable surfactants. At least about 5% to about 15% w/w or from about 6% to about 12% w/w of the pharmaceutical product may be stabilizing agent. In embodiments, intragranular excipients include about 6% stabilizing agent. In embodiments, intragranular excipients include about 12% stabilizing agent.

Fillers may include, for example, microcrystalline cellulose, such as Avicel® PH102, lactose monohydrate and other suitable fillers. At least about 15% to about 40% w/w or from about 20% to about 30% w/w of the pharmaceutical product may be filler. In embodiments, intragranular excipients include about 20% filler. In embodiments, intragranular excipients include about 24% filler. In embodiments, intragranular excipients include about 26% filler. In embodiments, intragranular excipients include about 30% filler. In embodiments, intragranular excipients include about 38% filler.

The filler of the pharmaceutical product may include a combination of fillers such as a combination of microcrystalline cellulose and lactose monohydrate. At least about 15% to about 25% w/w or from about 15% to about 20% w/w of the pharmaceutical product may be microcrystalline cellulose, and at least about 5% to about 20% w/w or from about 8% to about 10% w/w of the pharmaceutical product may be lactose monohydrate. In embodiments, intragranular excipients include about 20% microcrystalline cellulose and about 10% lactose monohydrate. In embodiments, intragranular excipients include about 23% microcrystalline cellulose and about 16% lactose monohydrate. In embodiments, intragranular excipients include about 20% microcrystalline cellulose and about 10% lactose monohydrate. In embodiments, intragranular excipients include about 18% microcrystalline cellulose and about 9% lactose monohydrate. In embodiments, intragranular excipients include about 17% microcrystalline cellulose and about 9% lactose monohydrate. In embodiments, intragranular excipients include about 16% microcrystalline cellulose and about 8% lactose monohydrate.

Alkalizing agents may include, for example, sodium carbonate, sodium bicarbonate, sodium arginine or any other suitable alkalizing agent in any suitable amounts including, for example, from about 2% to about 15% w/w or from about 5% to about 10% of the pharmaceutical product.

Surfactants may include, for example, polaxamers, such as Lutrol® F127, ethylene oxide/propylene oxide block copolymers, such as Pluronic® F68, sodium dodecyl sulfate or any other suitable surfactant. At least about 2% to about 5% w/w of the pharmaceutical product may be surfactant. In embodiments, intragranular excipients include about 3% surfactant.

Solvents may include aqueous and non-aqueous solvents. In embodiments the solvent is water in sufficient quantity.

Extragranular excipients may include one or more of fillers, alkalizing agents, disintegrants and lubricants, and any other suitable extragranular excipients and combinations thereof.

Fillers may include, for example, microcrystalline cellulose, such as Avicel® PH102, lactose monohydrate and other suitable fillers. At least about 5% to about 25% w/w or from about 10% to about 23% w/w of the pharmaceutical product may be filler. In embodiments, extragranular excipients include about 10% filler. In embodiments, extragranular excipients include about 13% filler. In embodiments, extragranular excipients include about 15% filler. In embodiments, extragranular excipients include about 18% filler. In embodiments, extragranular excipients include about 23% filler.

Disintegrants may include, for example, cross-linked sodium carboxymethylcellulose, such as sodium croscarmellose or any other suitable disintegrant in any suitable amounts including, for example, from about 1% to about 25% w/w or from about 2% to about 20% of the pharmaceutical product. In embodiments, extragranular excipients include about 2% disintegrant. In embodiments, extragranular excipients include about 5% disintegrant. In embodiments, extragranular excipients include about 10% disintegrant. In embodiments, extragranular excipients include about 20% disintegrant.

Lubricants may include, for example, sodium stearyl fumarate, colloidal silicon dioxide or any other suitable lubricant in any suitable amounts including, for example, from about 0.1% to about 15% w/w or from about 0.5% to about 5% of the pharmaceutical product. In embodiments, extragranular excipients include about 0.5% lubricant. In embodiments, extragranular excipients include about 2% lubricant. In embodiments, extragranular excipients include about 5% lubricant. In embodiments, extragranular excipients include about 5% lubricant.

The final blend may be compressed into tablets or encapsulated into capsules. In embodiments, the final blend is compressed into tablets using a rotary press, hydraulic press, such as a Carver press, or any other suitable compression mechanism. At least one additive selected from flow regulators, disintegrants, bulking agents and lubricants is preferably used in compacting the granules. Disintegrants promote a rapid disintegration of the compact in the stomach and keep the liberated granules separate from one another. Suitable disintegrants are crosslinked polymers such as crosslinked polyvinyl pyrrolidone and crosslinked sodium carboxymethyl cellulose. Suitable bulking agents are selected from lactose, calcium hydrogen phosphate, microcrystalline cellulose (Avicel®), magnesium oxide, natural or pre-gelatinized potato or corn starch, polyvinyl alcohol.

Suitable flow regulators are selected from highly dispersed silica (Aerosil®), and animal or vegetable fats or waxes.

A lubricant is preferably used in compacting the granules. Suitable lubricants are selected from polyethylene glycol (e.g., having a Mw of from 1000 to 6000), magnesium and calcium stearates, sodium stearyl fumarate, talc, and the like.

Various other additives may be used, for example dyes such as azo dyes, organic or inorganic pigments such as aluminum oxide or titanium dioxide, or dyes of natural origin; stabilizers such as antioxidants, light stabilizers, radical scavengers, or stabilizers against microbial attack.

Tablets may be coated with a suitable coating including enteric coating. In order to facilitate the intake of such a dosage form by a mammal, it is advantageous to give the dosage form an appropriate shape. Large tablets that can be swallowed comfortably are therefore preferably elongated rather than round in shape. A film coat on the tablet further contributes to the ease with which it can be swallowed. A film coat also improves taste and provides an elegant appearance. If desired, the film coat may be an enteric coat. The film coat usually includes a polymeric film-forming material such as (hydroxypropyl)methyl cellulose, hydroxypropyl cellulose, and acrylate or methacrylate copolymers. Besides a film-forming polymer, the film coat may further comprise a plasticizer, e.g. polyethylene glycol, a surfactant, e.g. a Tween® type, and optionally a pigment, e.g. titanium dioxide or iron oxides. The film-coating may also comprise talc as anti-adhesive. The film coat usually accounts for less than about 5% by weight of the dosage form.

Table 15 presents further examples of the disclosed formulations prepared by milling and wet granulation of the active agent with excipients and compressing the final blend into tablets. In particular, Table 15 presents the percentage of components by weight (w/w) of formulations of 100 mg dosages of the Compound A in tablet dosage forms.

TABLE 15

|  |  | Formulation | |
| --- | --- | --- | --- |
|  |  | 14 | 18 |
| Component | | % w/w | % w/w |
| Intra-granular | | | |
| Active Agent | Compound A | 26.6 | 26.6 |
| Polymer | Copovidone K28 | 8 | 8 |
| Surfactant | Vitamin E TPGS | 12 | 12 |
| Filler | Avicel ® PH 101 | 15.8 | 22.8 |
|  | Lactose monohydrate | 7.8 | 15.6 |
| Alkalizing Agent | Sodium Carbonate | 5 | 5 |
| Surfactant | Pluronic ® F68 | — | 3 |
| Solvent | Water | q.s. | q.s. |
| Extra-granular | | | |
| Filler | Avicel ® PH 102 | 17.8 | — |
| Disintegrant | Na Croscarmellose | 5 | 5 |
| Lubricant | Sodium Stearyl Fumarate | 2 | 2 |
| | Total | 100 | 100 |

In Vitro Dissolution Test

Figure 10:
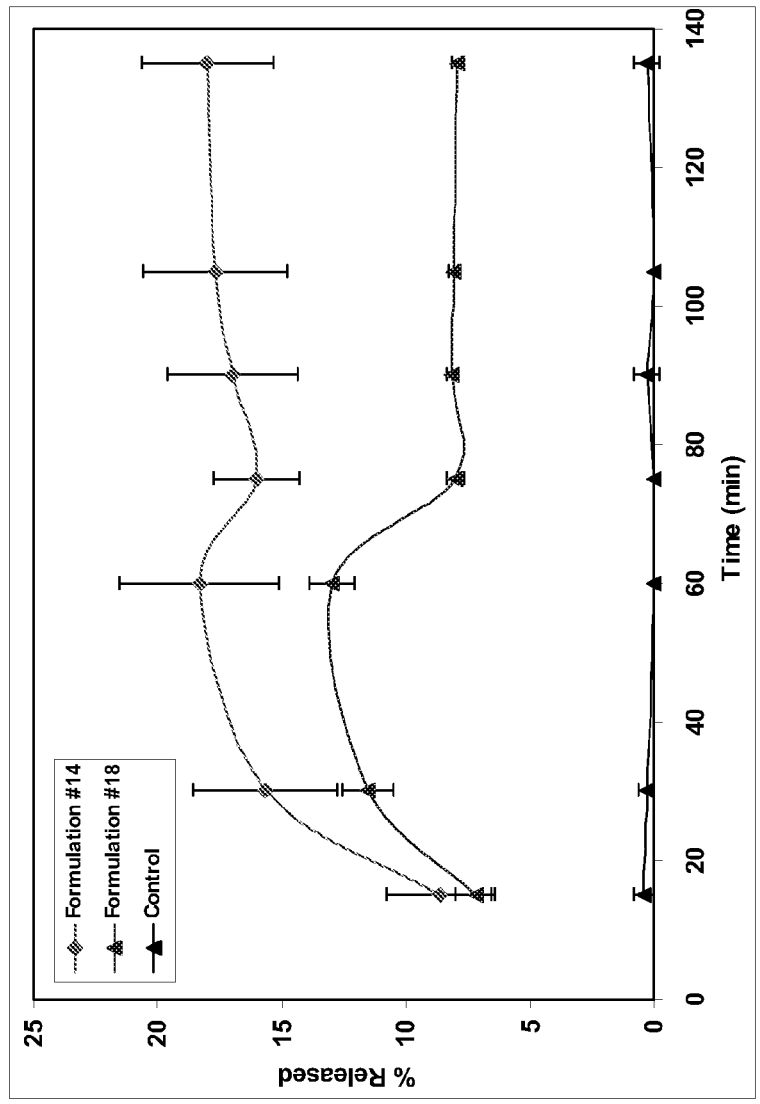
FIG. 10 is a graph illustrating in vitro release profiles of formulations prepared by Process II.

FIG. 10 illustrates in vitro drug release profiles of the tablet formulations prepared by Process II illustrated in FIG. 6. A control formulation was prepared by direct blending and compression of Compound A with Avicel® PH102, lactose monohydrate, sodium croscarmellose and sodium stearyl fumarate. The results demonstrate that dissolution rate and extent of drug released from each of the disclosed formulations are higher than those of the control formulation.

Packaging

In embodiments, the disclosed formulations are packaged in induction sealed high density polyethylene (HDPE) bottles with polypropylene caps. In embodiments, the disclosed formulations are further packaged within a cardboard carton to minimize photo-degradation.

Uncoated amorphous solid dispersion (ASD) tablets of phenyl uracil compounds of formula I have been found to be light sensitive when stored under regular light (up to UV-VIS range of 525 nm). About 8.86% light degradation product is formed when tablets are exposed under 2 times ICH photo condition. However, when tablets are coated, such as with dry color dispersion yellow 85F32450 (Opadry® II), and exposed under 2 times ICH photo condition, only about 0.68% light degradation product is formed. When in solution, Compound A may convert into an alternative isomer upon exposure to light; thus, in an embodiment, such solutions are stored under conditions that reduce exposure to light (e.g., in an amber bottle or in a dark place).

In embodiments, the disclosed pharmaceutical compositions comprise from about 0.001 to about 100 mg/kg, more preferably from about 10 mg to about 1000 mg of phenyl uracil compounds of formula I such as Compound A. In an embodiment, the amount of Compound A in a pharmaceutical composition is about 100 mg. In an embodiment, the amount of Compound A in a pharmaceutical composition is about 300 mg. In an embodiment, the amount of compound A in a pharmaceutical composition is about 400 mg. In an embodiment, the amount of Compound A in a pharmaceutical composition is about 600 mg.

Dosage unit compositions can contain such amounts or submultiples thereof to make up the daily dose. In many instances, the administration of the disclosed compositions will be repeated a plurality of times. Multiple doses per day typically may be used to increase the total daily dose, if desired. For example, the disclosed compositions may be administered at least three times daily (e.g., every 8 hours in a 24-hour period), at least two times daily (e.g., every 12 hours in a 24-hour period), at least once daily (e.g., once in a 24-hour period), and at least once weekly (e.g., once in a 7-day period)

The compositions optionally may comprise one or more additional therapeutic agents, such as, for example, another therapeutic agent used to treat hepatitis C (e.g., interferon or interferon/ribavirin combination, or an HCV inhibitor such as, for example, an HCV polymerase inhibitor or an HCV protease inhibitor). The disclosed compositions may also include therapeutic agents other than therapeutic agents used to treat hepatitis C (e.g., anti-HIV agents).

The disclosed formulations and compositions of phenyl uracil compounds of formula I or a pharmaceutically acceptable salt thereof, such as Compound A, may be used for treating a disorder by inhibiting replication of an RNA virus (including HCV), and treat a disease treatable by inhibiting HCV ribonucleic acid (RNA) polymerase (including hepatitis C). The disclosed formulations and compositions of phenyl uracil compounds of formula I or a pharmaceutically acceptable salt thereof, such as Compound A, may be used for inhibiting replication of an RNA virus. In embodiments, a disclosed pharmaceutical composition comprising compound A is exposed to the virus. In some embodiments, the RNA virus whose replication is being inhibited is a single-stranded, positive sense RNA virus. In embodiments, the RNA virus whose replication is being inhibited is a virus from the Flaviviridae family. In embodiments, the RNA virus whose replication is being inhibited is HCV.

The disclosed formulations and compositions of phenyl uracil compounds of formula I or a pharmaceutically acceptable salt thereof, such as Compound A, may be used for inhibiting HCV RNA polymerase. In embodiments, a disclosed pharmaceutical composition comprising compound A is exposed to the polymerase.

The term "inhibiting" means reducing the level of RNA virus replication/HCV polymerase activity. For example, if a pharmaceutical composition comprising compound A reduces the level of RNA virus replication by at least about 10% compared to the level of RNA virus replication before the virus was exposed to the pharmaceutical composition, then the compound/salt inhibits RNA virus replication. In some embodiments, the pharmaceutical composition can inhibit RNA virus replication by at least about 20%, at least about 30%, at least about 40%, at least about 50%, at least about 60%, at least about 70%, at least about 80%, at least about 90%, or at least about 95%.

The disclosed formulations and compositions of phenyl uracil compounds of formula I or a pharmaceutically acceptable salt thereof, such as Compound A, may be used for treating a disease that can be treated by inhibiting HCV RNA polymerase, such as hepatitis C. Thus, this disclosure is directed, in part, to a method of treating hepatitis C comprising administering to a subject in need thereof an effective amount of a disclosed formulation, and, optionally, one or more additional therapeutic agents. In embodiments, a therapeutically effective amount of a disclosed composition comprising Compound A is administered to the animal. "Treating" means ameliorating, suppressing, eradicating, preventing, reducing the risk of, and/or delaying the onset of the disease being treated. The term "treating" encompasses administration of the compounds and/or salts of the invention to an HCV-negative patient that is a candidate for an organ transplant. The methods of treatment are particularly suitable for use with humans, but may be used with other animals, particularly mammals. A "therapeutically-effective amount" or "effective amount" is an amount that will achieve the goal of treating the targeted condition.

In some embodiments, the methods comprise combination therapy, wherein the disclosed compositions are co-administered with a second (or even a third, fourth, etc.) compound, such as, for example, another therapeutic agent used to treat hepatitis C (e.g., interferon or interferon/ribavirin combination, or an HCV inhibitor such as, for example, an HCV polymerase inhibitor or an HCV protease inhibitor). The disclosed compositions may also be co-administered with therapeutic agents other than therapeutic agents used to treat hepatitis C (e.g., anti-HIV agents). In embodiments, the disclosed composition is co-administered with an HCV inhibitor.

In these co-administration embodiments, the disclosed compositions and the second, etc. therapeutic agent(s) may be administered in a substantially simultaneous manner (e.g., or within about 5 minutes of each other), in a sequential manner, or both. It is contemplated that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. The disclosed compositions and the second, etc. therapeutic agent may also be administered in a single formulation.

This disclosure also is directed, in part, to use of the disclosed compositions, and, optionally one or more additional therapeutic agents to prepare a medicament. In some embodiments, the medicament is for co-administration with one or more additional therapeutic agents.

In some embodiments, the medicament is for inhibiting replication of an RNA virus.

In some embodiments, the medicament is for treating hepatitis C.

This disclosure also is directed, in part, to the disclosed compositions, and, optionally one or more additional therapeutic agents, for use as a medicament. In some embodiments, the medicament is for inhibiting replication of an RNA virus. In other embodiments, the medicament is for treating hepatitis C. In some embodiments, the compositions further comprise one or more additional therapeutic agents such as additional HCV inhibitors.

As used throughout this specification and the appended claims, the following terms have the following meanings:

The term "alkyl" (alone or in combination with another term(s)) means a straight- or branched-chain saturated hydrocarbyl substituent typically containing from 1 to about 20 carbon atoms, more typically from 1 to about 8 carbon atoms, and even more typically from 1 to about 6 carbon atoms. Examples of such substituents include methyl, ethyl, n-propyl, isopropyl, n-butyl, isobutyl, sec-butyl, tert-butyl, pentyl, iso-amyl, and hexyl. As in this definition, throughout this detailed description Applicants have provided illustrative examples. The provision of such illustrative examples should not be interpreted as if the provided illustrative examples are the only options available to one skilled in the art.

The term "alkenyl" (alone or in combination with another term(s)) means a straight- or branched-chain hydrocarbyl substituent containing one or more double bonds and typically from 2 to about 20 carbon atoms, more typically from about 2 to about 8 carbon atoms, and even more typically from about 2 to about 6 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl.

The term "alkynyl" (alone or in combination with another term(s)) means a straight- or branched-chain hydrocarbyl substituent containing one or more triple bonds and typically from 2 to about 20 carbon atoms, more typically from about 2 to about 8 carbon atoms, and even more typically from about 2 to about 6 carbon atoms. Examples of such substituents include ethynyl, 2-propynyl, 3-propynyl, 2-butynyl, and 3-butynyl.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single ring, which typically contains from 3 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl alternatively may be 2 or 3 rings fused together, such as naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 6 carbon ring atoms. Examples of single-ring cycloalkyls include cyclopropyl, cyclobutyl, cyclopentyl, and cyclohexyl. A cycloalkyl alternatively may be 2 or 3 carbon rings fused together, such as, decalinyl.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

The term "hydrogen" (alone or in combination with another term(s)) means a hydrogen radical, and may be depicted as —H.

The term "hydroxy" (alone or in combination with another term(s)) means —OH.

The term "cyano" (alone or in combination with another term(s)) means —CN, which also may be depicted as —C≡N.

The term "keto" (alone or in combination with another term(s)) means an oxo radical, and may be depicted as =O.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl alternatively may be 2 or 3 rings fused together, such as, for example, indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

The term "haloalkyl" (alone or in combination with another term(s)) means an alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "nitrogen-protecting group" as means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

The term "oxo" (alone or in combination with another term(s)) means a =O group.

A prefix attached to a multi-component substituent only applies to the first component. To illustrate, the term "alkylcycloalkyl" contains two components: alkyl and cycloalkyl. Thus, the $C_1$-$C_6$- prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkoxyalkyl indicates that only the alkoxy component of the alkoxyalkyl substituent is substituted with one or more halogen radicals. If halogen substitution may alternatively or additionally occur on the alkyl component, the substituent would instead be described as "halogen-substituted alkoxyalkyl" rather than "haloalkoxyalkyl." And finally, if the halogen substitution may only occur on the alkyl component, the substituent would instead be described as "alkoxyhaloalkyl."

If substituents are described as being "independently selected" from a group, each substituent is selected independent of the other. Each substituent therefore may be identical to or different from the other substituent(s).

When words are used to describe a substituent, the rightmost-described component of the substituent is the component that has the free valence.

When a chemical formula is used to describe a substituent, the dash on the left side of the formula indicates the portion of the substituent that has the free valence.

When a chemical formula is used to describe a linking element between two other elements of a depicted chemical structure, the leftmost dash of the substituent indicates the portion of the substituent that is bound to the left element in the depicted structure. The rightmost dash, on the other hand, indicates the portion of the substituent that is bound to the right element in the depicted structure. To illustrate, if the depicted chemical structure is X-L-Y and L is described as —C(O)—N(H)—, then the chemical would be X—C(O)—N(H)—Y.

With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below.

The term "amorphous" as applied to a compound refers to a solid-state in which the compound molecules are present in a disordered arrangement and do not form a distinguishable crystal lattice or unit cell. When subjected to X-ray powder diffraction, an amorphous compound does not produce any characteristic crystalline peaks.

The term "crystalline form" as applied to a compound refers to a solid-state in which the compound molecules are arranged to form a distinguishable crystal lattice (i) comprising distinguishable unit cells, and (ii) yielding diffraction pattern peaks when subjected to X-ray radiation.

The term "purity", unless otherwise qualified, means the chemical purity of a compound according to conventional HPLC assay.

The term "phase purity" means the solid-state purity of a compound with regard to a particular crystalline or amorphous form of the compound as determined by X-ray powder diffraction analytical methods.

The term "phase pure" refers to purity with respect to other solid-state forms of the compound, and does not necessarily imply a high degree of chemical purity with respect to other compounds.

The term "PXRD" or XPRD means X-ray powder diffraction.

The term "TGA" means thermogravimetric analysis.

The term "DSC" means differential scanning calorimetry.

INCORPORATION BY REFERENCE

As used throughout this specification and the appended claims, the following abbreviations have the following meanings:

API means active pharmaceutical intermediate.

ASD means amorphous solid dispersion.

AUC means area under the curve.

CoPVP means vinylpyrrolidone-vinyl acetate copolymer.

HDPE means high-density polyethylene

HPC means hydroxypropyl cellulose.

HPLC means high performance liquid chromatography.

HPMC means (hydroxypropyl)methyl cellulose.

ICH means International Conference on Harmonisation.

MS means mass spectrum.

PVP means vinylpyrrolidone polymer.

SDS means sodium dodecyl sulfate.

TPGS means d-alpha tocopheryl polyethylene glycol succinate.

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A pharmaceutical product comprising an amorphous solid dispersion comprising an active agent compound having the structure of formula I or a salt thereof

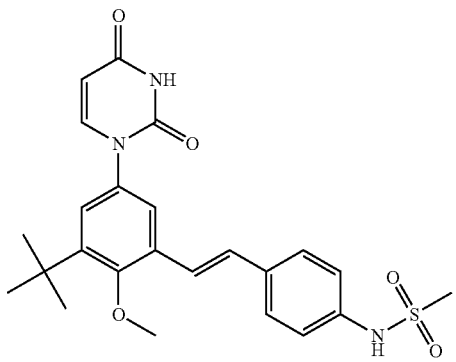

2. The pharmaceutical product of claim 1, wherein the active agent compound is a potassium salt of (E)-N-(4-(3-tert-butyl-5-(2,4-dioxo-3,4-dihydro-pyrimidin-1(2H)-yl)-2-methoxystyryl)phenyl)methanesulfonamide.

3. The pharmaceutical product of claim 1, further comprising at least one polymer and at least one surfactant.

4. The pharmaceutical product of claim 3, wherein the polymer is selected from the group consisting of copovidone, polyvinylpyrrolidone, (hydroxypropyl)methyl cellulose, and hydroxypropyl cellulose.

5. The pharmaceutical product of claim 3, wherein the surfactant is selected from the group consisting of vitamin E d-alpha tocopheryl polyethylene glycol succinate, sorbitan laurate and polyoxyethylene sorbitan monolaurate.

6. The pharmaceutical product of claim 1, wherein said product comprises an amorphous solid dispersion comprising of a potassium salt of (E)-N-(4-(3-tert-butyl-5-(2,4-dioxo-3,4-dihydro-pyrimidin-1(2H)-yl)-2-methoxystyryl)phenyl)methanesulfonamide, a polymer and a surfactant.

7. The pharmaceutical product of claim 1, wherein the product is obtained by
  a) preparing a liquid mixture comprising the active agent compound; at least one polymer; at least one surfactant; and at least one solvent;
  b) removing the solvent from the liquid mixture to form a solid dispersion;
  c) combining the solid dispersion with at least one pharmaceutically acceptable excipient.

8. A pharmaceutical product comprising an active agent compound having the structure of formula I, a salt thereof, or a crystal form thereof

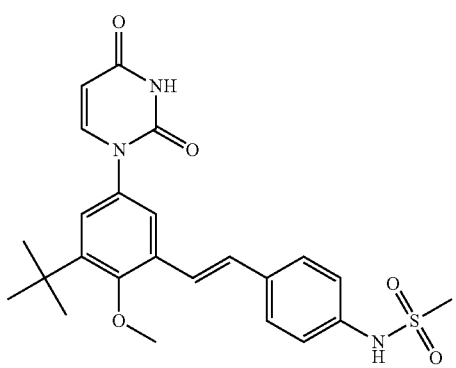

at least one polymer, at least one alkalizing agent, and at least one surfactant, wherein the at least one alkalizing agent is selected from the group consisting of sodium carbonate, sodium bicarbonate, and sodium arginine.

9. The pharmaceutical product of claim 8, wherein the polymer is selected from the group consisting of copovidone, polyvinylpyrrolidone, (hydroxypropyl)methyl cellulose, and hydroxypropyl cellulose.

10. The pharmaceutical product of claim 8, wherein the surfactant is selected from the group consisting of vitamin E d-alpha tocopheryl polyethylene glycol succinate, sorbitan laurate and polyoxyethylene sorbitan monolaurate.

11. The pharmaceutical product of claim 8, wherein the active agent is combined with at least one pharmaceutically acceptable excipient by a process comprising
  a) dissolving at least one polymer, at least one stabilizing agent and at least one surfactant to form a granulation fluid;
  b) mixing the active agent with the granulation fluid and at least one alkalizing agent to form an intragranular portion of the pharmaceutical product; and
  c) blending the intragranular portion of the pharmaceutical product with at least one additional excipient.

12. The pharmaceutical product of claim 11, wherein the active agent is combined with the pharmaceutically acceptable excipient by milling and wet-granulation.

13. The pharmaceutical product of claim 12, wherein the milling and wet granulation process comprises milling the active agent together with an alkalizing agent and at least one filler and suspending in a fluid to form a coating suspension.

14. The pharmaceutical product of claim 1, wherein the pharmaceutical product is a tablet.

15. A method for preparing a pharmaceutical product comprising an active agent, potassium salt of (E)-N-(4-(3-tert-butyl-5-(2,4-dioxo-3,4-dihydro-pyrimidin-1(2H)-yl)-2-methoxystyryl)phenyl) methanesulfonamide, said method comprising:
  a) preparing a liquid mixture comprising the active agent compound; at least one polymer; at least one surfactant; and at least one solvent;
  b) removing the solvent from the liquid mixture to form a solid dispersion;
  c) combining the solid dispersion with at least one pharmaceutically acceptable excipient.

16. A method for preparing a pharmaceutical product comprising an active agent, potassium salt of (E)-N-(4-(3-tert-butyl-5-(2,4-dioxo-3,4-dihydro-pyrimidin-1(2H)-yl)-2-methoxystyryl)phenyl) methanesulfonamide, said method comprising:
  a) dissolving at least one polymer, at least one stabilizing agent and at least one surfactant to form a granulation fluid;
  b) mixing the active agent with the granulation fluid and at least one alkalizing agent to form an intragranular portion of the pharmaceutical product; and
  c) blending the intragranular portion of the pharmaceutical product with at least one additional excipient.

17. The method of claim 15, further comprising compressing the solid dispersion product to obtain a tablet.

\* \* \* \* \*